(12) United States Patent
Gabbay

(10) Patent No.: US 6,869,444 B2
(45) Date of Patent: Mar. 22, 2005

(54) LOW INVASIVE IMPLANTABLE CARDIAC PROSTHESIS AND METHOD FOR HELPING IMPROVE OPERATION OF A HEART VALVE

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 26 days.

(21) Appl. No.: 10/215,800

(22) Filed: Aug. 9, 2002

(65) Prior Publication Data

US 2003/0199975 A1 Oct. 23, 2003

Related U.S. Application Data

(63) Continuation-in-part of application No. 10/204,316, filed as application No. PCT/US01/14620 on May 7, 2001, and a continuation of application No. 09/575,880, filed on May 22, 2000, now Pat. No. 6,419,695.

(51) Int. Cl.[7] .................................................. A61F 2/06
(52) U.S. Cl. ...................................... 623/2.36; 128/898
(58) Field of Search ............................... 623/2.11–2.39

(56) References Cited

U.S. PATENT DOCUMENTS

| | | |
|---|---|---|
| 4,042,979 A | 8/1977 | Angell |
| 4,084,268 A | 4/1978 | Ionescu et al. |
| 4,240,161 A | 12/1980 | Huffstutler et al. |
| 4,350,492 A | 9/1982 | Wright et al. |
| 4,477,930 A | 10/1984 | Totten et al. |
| 4,491,986 A | 1/1985 | Gabbay |
| 4,725,274 A | 2/1988 | Lane et al. |
| 4,759,758 A | 7/1988 | Gabbay |
| 5,258,021 A | 11/1993 | Duran |
| 5,411,552 A | 5/1995 | Andersen et al. |
| 5,500,014 A | 3/1996 | Quijano et al. |
| 5,549,665 A | 8/1996 | Vesely et al. |
| 5,554,185 A * | 9/1996 | Block et al. ............... 623/2.12 |
| 5,584,879 A | 12/1996 | Reimold et al. |
| 5,800,527 A | 9/1998 | Jansen et al. |
| 5,840,081 A | 11/1998 | Andersen et al. |
| 5,855,601 A * | 1/1999 | Bessler et al. ............. 623/2.38 |
| 5,855,602 A | 1/1999 | Angell |
| 5,861,028 A | 1/1999 | Angell |
| 5,948,017 A | 9/1999 | Taheri |
| 6,168,614 B1 | 1/2001 | Andersen et al. |
| 6,419,695 B1 | 7/2002 | Gabbay |
| 2003/0083742 A1 * | 5/2003 | Spence et al. ............. 623/2.16 |

FOREIGN PATENT DOCUMENTS

| | | | |
|---|---|---|---|
| EP | 0850607 | 7/1998 | |
| WO | WO 92/13502 | * 8/1992 | ............. A61F/2/24 |

OTHER PUBLICATIONS

"Nitinol Solutions", Product brochure of Raychem Corporation, Electronics OEM Components Division Menlo Park, California Copyright date of 1999.

* cited by examiner

*Primary Examiner*—Thomas Barrett
(74) *Attorney, Agent, or Firm*—Tarolli, Sundheim, Covell & Tummino L.L.P.

(57) ABSTRACT

An apparatus for helping improve operation of a heart valve includes a generally arcuate base and a buttress extending generally from at least a portion of the base. The apparatus can be deformable to facilitate its implantation. When the apparatus is when implanted at an annulus of a heart valve, the buttress thereof cooperates with one or more leaflets of the heart valve to help control blood flow relative to the apparatus and heart valve.

31 Claims, 10 Drawing Sheets

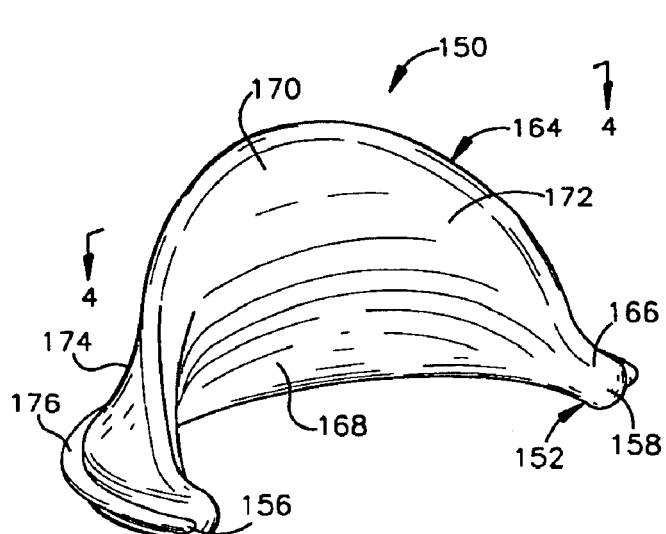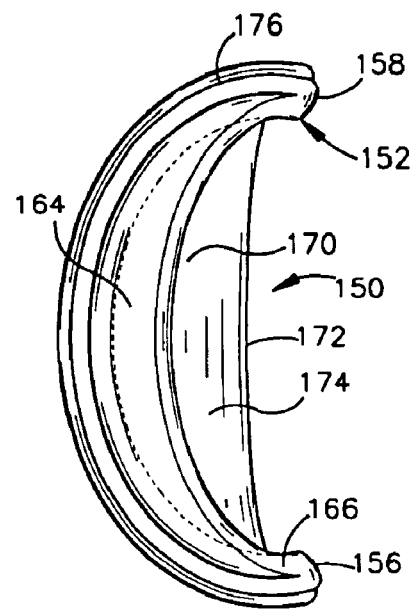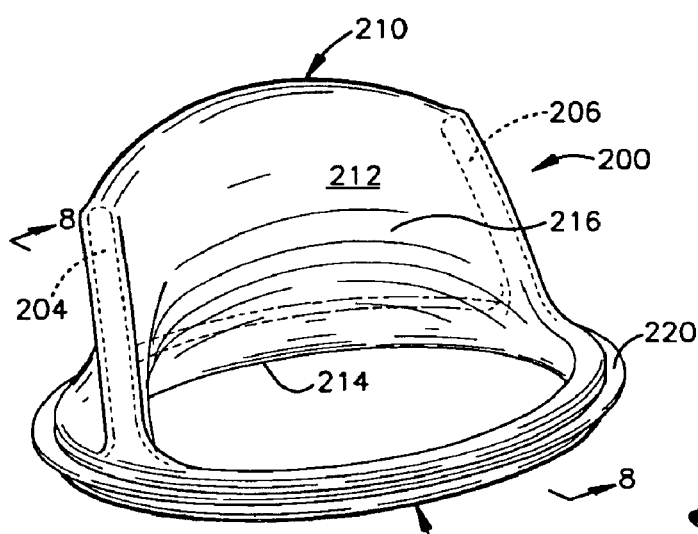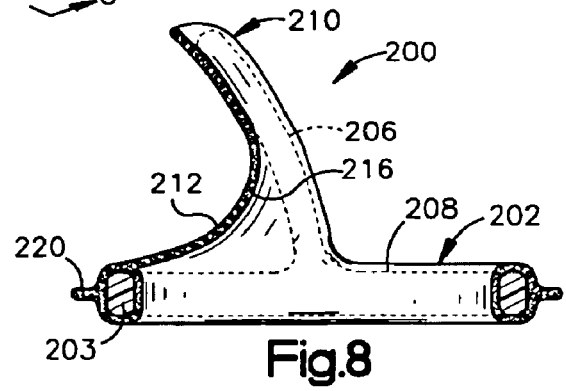

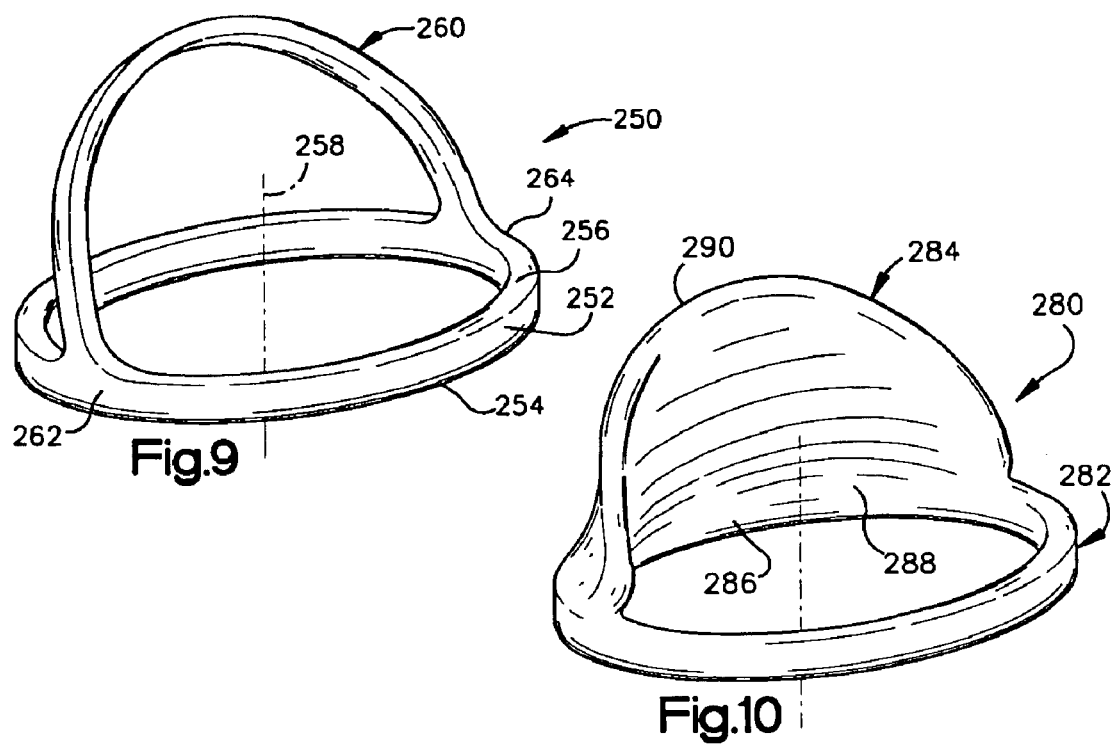
Fig.9
Fig.10
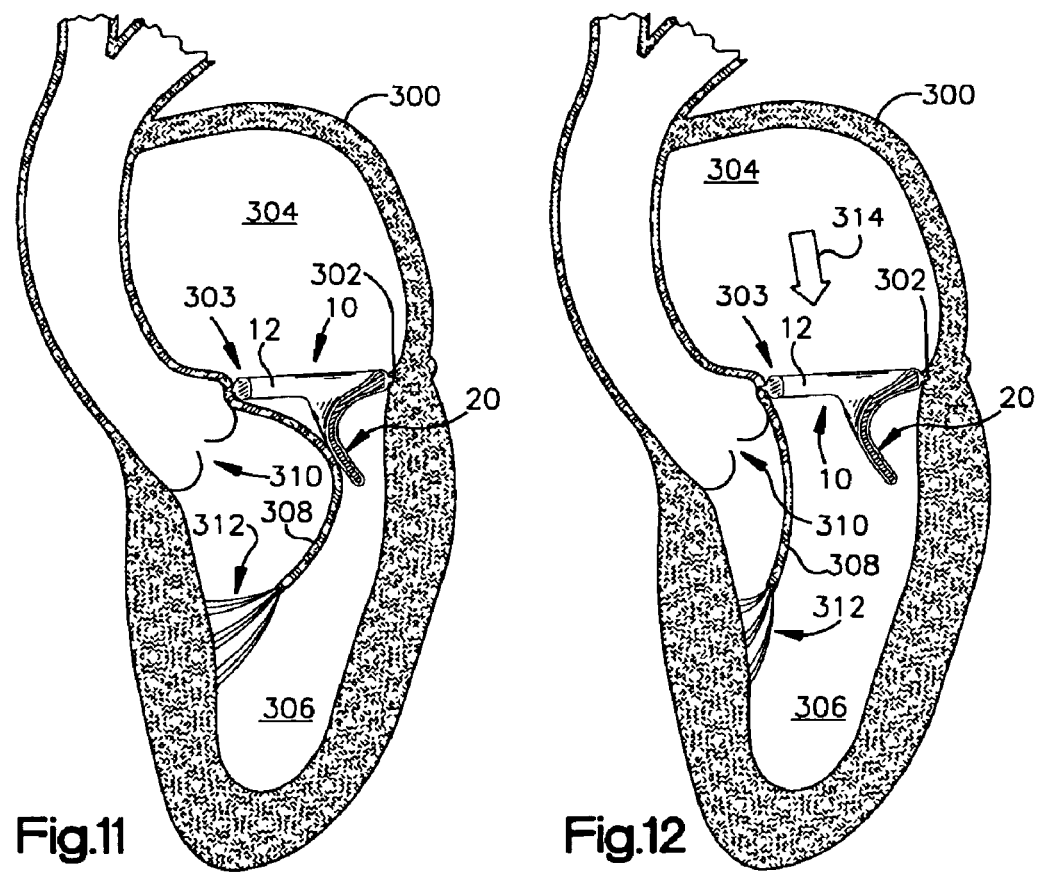
Fig.11
Fig.12

LOW INVASIVE IMPLANTABLE CARDIAC PROSTHESIS AND METHOD FOR HELPING IMPROVE OPERATION OF A HEART VALVE

REFERENCE TO RELATED APPLICATIONS

This application is a continuation-in-part of U.S. patent application Ser. No. 10/204,316, which was filed on Aug. 20, 2002, and entitled METHOD FOR HELPING IMPROVE OPERATION OF A HEART VALVE, which is a 371 of PCT/US01/14620 filed May 7, 2001, and a continuation of U.S. patent application Ser. No. 09/575,880, which was filed May 22, 2000, now U.S. Pat. No. 6,419,695, and entitled CARDIAC PROSTHESIS FOR HELPING IMPROVE OPERATION OF A HEART VALVE, all of which are incorporated herein by reference.

TECHNICAL FIELD

The present invention relates to an implantable cardiac prosthesis and, more particularly, to a prosthesis that can be implanted using generally low invasive techniques at an annulus of a heart valve to help improve its operation.

BACKGROUND

A heart valve may become defective or damaged, such as resulting from congenital malformation, disease, or aging. When the valve becomes defective or damaged, the leaflets may not function properly. One common problem associated with a degenerating heart valve is an enlargement of the valve annulus (e.g., dilation). Other problems that may result in valve dysfunction are chordal elongation and lesions developing on one or more of the leaflets.

The bicuspid or mitral valve is located in the left atrio-ventricular opening of the heart for passing blood unidirectionally from the left atrium to the left ventricle of the heart. The mitral valve is encircled by a dense fibrous annular ring and includes two valve leaflets of unequal size. A larger valve leaflet, which is known as the anterior leaflet, is located adjacent the aortic opening. The smaller leaflet is the posterior leaflet.

When a mitral valve functions properly, for example, it prevents regurgitation of blood from the ventricle into the atrium when the ventricle contracts. In order to withstand the substantial backpressure and prevent regurgitation of blood into the atrium during the ventricular contraction, the cusps are held in place by fibrous cords (cordae tendinae) that anchor the valve cusps to the muscular wall of the heart.

By way of example, if an annulus enlarges or dilates to a point where the attached leaflets are unable to fully close (malcoaptation), regurgitation or valve prolapse may occur. Adverse clinical symptoms, such as chest pain, cardiac arrythmias, or dyspnea, may manifest in response to valve prolapse or regurgitation. As a result, surgical correction, either by valve repair procedures or by valve replacement, may be required.

Surgical reconstruction or repair procedures may include plication, chordal shortening, or chordal replacement. Another common repair prodecure relates to remodelling of the valve annulus (e.g., annuloplasty), which may be accomplished by implantation of a prosthetic ring to help stabilize the annulus and to correct or help prevent valvular insufficiency which may result from defect or dysfunction of the valve annulus. Properly sizing and implanting the annuloplasty ring can substantially restore the valve annulus to its normal, undilated circumference. In situations where the valve leaflets exhibit lesions, it also may be necessary to reconstruct one or more valve leaflets by securing grafts or patches to the leaflets, such as over lesions or holes formed in the leaflet. The repair or reconstruction of the leaflets may be complicated and time consuming, the results of which are not readily reproducible.

SUMMARY

The present invention relates generally to a cardiac prosthesis that may be implanted at an annulus of a heart valve to help improve operation of a defective or damaged valve. The prosthesis provides a buttress that extends from a generally arcuate base portion, such as in a radially inwardly and generally axially direction relative to the base portion. For example, the base portion could be generally C-shaped or annular.

The apparatus is formed of a material that can be manipulated to a reduced cross-sectional condition to facilitate its implantation. For example, the apparatus may be positioned in a generally cylindrical barrel or other enclosure such that the prosthesis has a reduced cross-sectional condition generally corresponding to an internal condition of the barrel. The barrel, which can be part of a catheter system or other implantation device, can then be utilized to position the apparatus at a desired position in a patient's heart and the apparatus discharged from the barrel. Upon being discharged, the apparatus can expand from the reduced cross-sectional condition to an expanded cross-sectional condition, such that an exterior portion of the base engages adjacent tissue of the patient's heart, such as at an annulus of the patient's defective or damaged heart valve, to mitigate axial movement of the apparatus relative to the adjacent tissue. The implantation can be performed with or without cardiopulmonary bypass. For example, to reduce the invasiveness of the procedure, the implantation of the apparatus further could be performed without opening the patient's heart. Another alternative would be to implant the apparatus directly through the patient's heart muscle.

When the apparatus is implanted at an annulus of a heart valve, the buttress provides a surface against which one or more leaflets of the patient's heart valve may move into and out of engagement. When the leaflet engages or coapts with the buttress, flow of blood through the valve is inhibited, thereby mitigating regurgitation. The apparatus also permits the flow of blood through patient's valve as the leaflet is urged away from the buttress.

To help anchor the buttress relative to the adjacent tissue, the base of the apparatus can include a plurality of radially extending features, such as spikes. The protrusions will help grip the surrounding tissue after expanding to its enlarged cross-sectional dimension, such as when discharged from the barrel.

To the accomplishment of the foregoing and related ends, the invention, then, comprises the features hereinafter fully described and particularly pointed out in the claims. The following description and the annexed drawings set forth in detail certain illustrative aspects of the invention. These aspects are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 5 is an isometric view of an apparatus for supporting a heart valve in accordance with another aspect of the present invention.

FIG. 6 is a view of the apparatus taken along line 6—6 of FIG. 5.

FIG. 7 is an isometric view of an apparatus in accordance with another aspect of the present invention.

FIG. 8 is a cross-sectional view of the apparatus taken along line 8—8 of FIG. 7.

FIG. 9 is an isometric view of a support frame for an apparatus in accordance with another aspect of the present invention.

FIG. 10 is an isometric view of an apparatus in accordance with another aspect of the present invention, which also may be employed as a frame for an apparatus.

FIG. 11 is a cross-sectional view of part of a heart in which an apparatus, in accordance with the present invention, is mounted at a heart valve, illustrating a first condition of the heart valve.

FIG. 12 is a cross-sectional view of the heart and apparatus, similar to FIG. 11, illustrating a second condition of the heart valve.

DESCRIPTION

Figure 1:
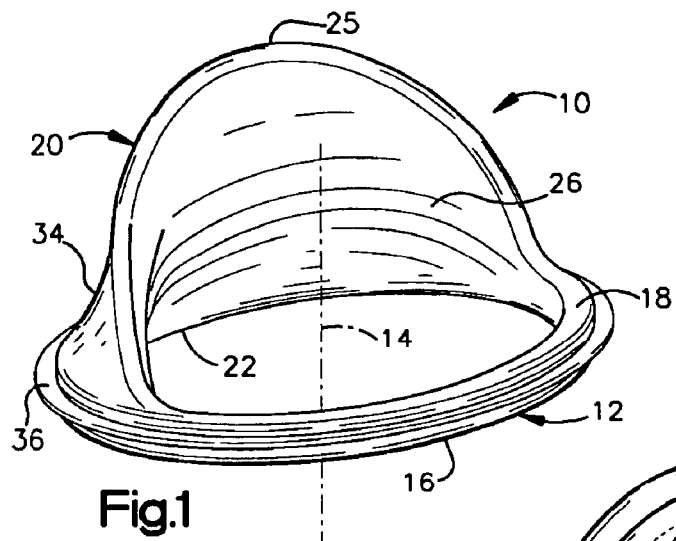
FIG. 1 is an isometric view of an apparatus in accordance with an aspect of the present invention.
Figure 2:
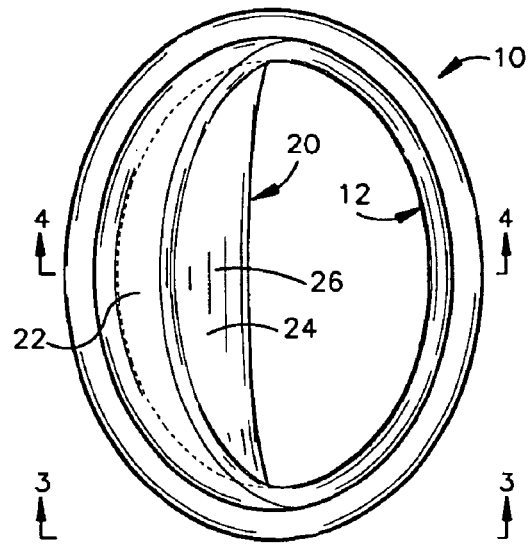
FIG. 2 is an outflow view of an apparatus in accordance with an aspect the present invention.

The present invention relates generally to a cardiac prosthesis that cooperates with a patient's heart valve to help improve operation of the patient's heart. The prosthesis can be manipulated to a reduced cross-sectional dimension, such as within an enclosure, to facilitate its positioning during implantation, and then removed from the housing to permit expansion to an expanded cross-sectional dimension at the implantation site. Such an approach can be utilized, for example, where it is desirable to implant the prosthesis in a generally minimally invasive manner, such as through a catheter or other implantation device. The invasiveness further can be reduced by performing the procedure with little or no cardio-pulmonary bypass.

FIGS. 1–4 illustrate an apparatus 10, in accordance with an aspect of the present invention, for helping to improve operation of a heart valve. The apparatus 10 includes a generally annular base portion 12, which may be an oval shape, egg-shaped or another suitable shape dimensioned and configured for attachment at an annulus of a heart valve. A central axis 14 extends through the apparatus 10 substantially transverse to a plane extending through the base portion 12. The base portion 12 has an inflow side 16 and an outflow side 18.

The base portion 12 may be formed of a generally rigid or flexible material, such as depending on the desired amount of support for a valve annulus to which the apparatus 10 is to be mounted. For example, the base portion 12 may be a plastic-like material, a metal or other material suitable for implantation into a patient. The base portion 12 provides the benefits of an annuloplasty ring (e.g., it helps support a valve annulus at a desired orientation at systole).

The apparatus 10 also includes a buttress 20 that is attached to and extends from the base portion 12 for providing a surface against which a leaflet of a heart valve may engage. The buttress 20 is connected to the base portion 12 along a circumferentially extending arc length of the base portion. The arc length of the base portion 12 may approximate the length of annular, attachment for a defective or damaged valve leaflet for which the buttress 20 (when the apparatus is implanted) is intended to function.

By way of example, when the apparatus 10 is to be implanted at the annulus of a mitral valve and function in place of a posterior leaflet, the circumferential arc may approximate the length of the annulus adjacent the posterior leaflet of the valve. Additionally, the circumferential length of the sidewall of the buttress 20 approximates the posterior leaflet.

Figure 3:
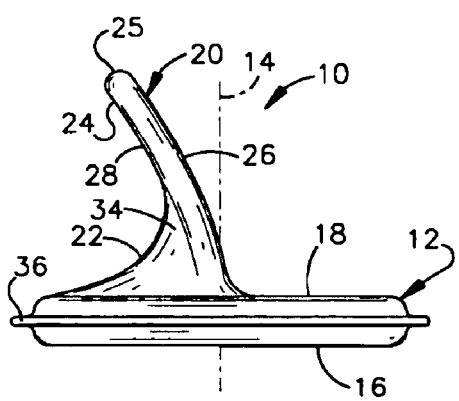
FIG. 3 is a side elevation of an apparatus for supporting a heart valve in accordance with an aspect the present invention, taken along line 3—3 of FIG. 2.
Figure 4:
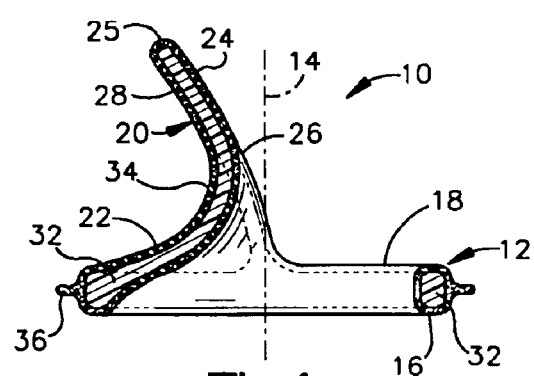
FIG. 4 is a cross-sectional view of the apparatus taken along line 4—4 of FIG. 2.

The buttress 20 extends generally axially from and radially outwardly relative to the outflow side 18 of the base portion 12. An axial length of a portion 22 of the buttress 20 proximal the base portion 12 extends radially inwardly toward the axis 14 and generally axially away from the base portion. A distally extending portion 24 of the buttress 20 extends from the proximal portion 22 and curves radially outwardly therefrom for the remaining length of the buttress to terminate in a distal end 25. The buttress 20 has a radially inner surface 26 that provides a surface against which a leaflet (e.g., an anterior leaflet of a mitral valve) may coapt at systole. As shown in FIGS. 3 and 4, a radially outer surface 28 of the buttress 20 at the distally extending portion 24 has a generally convex or an inverted C-shaped cross-section.

In the example of the apparatus 10 shown in FIGS. 1–4 (having a complete annular base portion 12), an aperture extends axially through the apparatus 10 between another arc length of the base portion 12 and the buttress itself. The aperture provides an opening or orifice to permit the passage of blood through the apparatus 10, such as during diastole. The buttress 20 in conjunction with the leaflet (or leaflets) also inhibits the flow of blood when the valve is in a closed position, such as during ventricular contraction at systole.

The apparatus 10 shown in FIGS. 1–4 includes a support frame 32 that is dimensioned and configured to provide a desired shape for the apparatus 10. The frame 32 provides a support mechanism that forms the base portion 12 and the buttress 20. The frame 32, for example, may be formed of a resilient and/or flexible material, such as a plastic, metal or other material suitable for implantation into a human. The rigidity or flexibility of each part of the frame may vary depending upon the amount of support desired at the annulus (by the base portion) as well as the amount of flexibility desired during engagement between a leaflet and the buttress 20.

Alternatively, the underlying support frame 32 of the buttress 20 and/or the base portion 12 may be formed of a substantially inelastically deformable material (e.g., it is bendable to and remains at a desired position), such as a metal wire. As a result, a surgeon implanting the apparatus 10 may reorient the buttress 20 and/or the base portion 12 to a desired configuration for improving the operation of the valve. Such material also may exhibit sufficient resilience so that it maintains the shape set by the surgeon (or manufacturer) after being implanted and subjected to the dynamics of the heart valve.

In accordance with another aspect of the present invention, the support frame 32 can be sufficiently flexible and resilient to permit the apparatus 10 to be compressible to a reduced cross-sectional dimension during positioning and then expand (e.g., automatically or upon being stimulated) to an increased cross-sectional dimension. For example, the apparatus can be implanted within a barrel of an implantation device, such as a catheter for implantation through a vessel or an implantation system generally linear, which can be utilized to implant the apparatus under direct or hidden vision of the surgeon.

The frame parts for the base portion 12 and the buttress 20 may be formed of the same or different materials depending on the material properties (elasticity, rigidity, resilience, etc.) desired for each part of the apparatus 10.

An outer sheath 34 of a biocompatible material covers the frame 32, including the base portion 12 and the buttress 20. The outer sheath 34 may be substantially any material, such as a cloth-like or fabric material (natural or synthetic), a biological material, such as collagen or an animal tissue material. An acceptable animal tissue material is smooth animal pericardium (e.g., equine, bovine, porcine, etc.) that has been tanned or fixed in a suitable tanning environment. The pericardium, for example, is cross-linked with glutaraldehyde and undergoes a detoxification process with heparin bonding, such as one of the NO-REACT® natural tissue products that are commercially available from Shelhigh, Inc. of Millburn, N.J. The NO-REACT® natural tissue products exhibit improved biocompatibility and mitigate calcification and thrombus formation. The exposed smooth animal pericardium covering the buttress 20 further inhibits abrasion that could occur in response to engagement between a leaflet and the buttress.

The apparatus 10 also may include an implantation flange 36 (or sewing ring) that circumscribes the base portion of the apparatus 10. The implantation flange 36 extends radially outwardly from the base portion 12 and provides a structure for facilitating implantation of the apparatus 10 at an annulus of a heart valve. The implantation flange 36 is formed of a flexible material, such a cloth-like or fabric material (natural or synthetic), a biological material, such as collagen, or an animal tissue material. For example, the implantation flange 36 is formed of a substantially biocompatible biological material, such as animal tissue (e.g., animal pericardium). The implantation flange 36 may be formed as an integral part of the outer sheath 34, such as a single or double layer of the material that is used to form the outer sheath.

FIGS. 5 and 6 illustrate a heart valve repair apparatus 150 in accordance with another aspect of the present invention. The apparatus 150 includes a generally annular base portion 152 that is generally C-shaped (or incomplete). The base portion 152 has ends 156 and 158 that are spaced apart from each other and a curved portion extending between the ends. In this example, the base portion 152 includes an underlying C-shaped support ring, which may be formed of a flexible, resilient, or generally rigid material. The support ring may have an elastic property so as to return to its original shape when deflected from its original (or rest) condition. The support ring for example, may be a plastic-like material (e.g., a polymer, a resin, etc.) or a metal (e.g., stainless steel), such as in the form of a wire. It will be understood and appreciated that other types of generally rigid, elastic, and/or resilient materials also may be used in accordance with the present invention. In addition, a suitable inelastically deformable material also could be used to form the support ring.

A buttress 164 extends generally axially from an outflow side 166 of the base portion 152 in a manner that is substantially similar to that shown and described with respect to FIGS. 1–4. Briefly stated, a proximal portion 168 of the buttress 164 extends generally axially and radially inward from the base portion 152 toward an open end (between ends 156 and 158) of the base portion. A distally extending portion 170 of the buttress 164 extends from the proximal portion 168 and curves radially outwardly therefrom for the remaining length of the buttress. The buttress 164 has a radially inner surface 172 that provides a surface against which a leaflet (e.g., an anterior leaflet of a mitral valve) may coapt at systole. The buttress 164 is dimensioned and configured to simulate the dimensions and configuration of a leaflet at systole so that, when the apparatus 150 is implanted at an annulus of a heart valve, a leaflet (or leaflets) may engage the buttress 164 to close the valve at systole. The leaflet (or leaflets) is able to coapt with the inner surface 172 of the buttress 164 at systole, thereby inhibiting regurgitation of blood when the ventricle contracts.

As in the example of FIGS. 1–4, the apparatus 150 also includes an outer sheath 174 of a flexible, biocompatible material covering the apparatus. The apparatus 150 also may include an implantation flange 176 (or sewing ring) that circumscribes the base portion 152 of the apparatus. The implantation flange 176 extends radially outwardly from the base portion 12 between the ends 156 and 158 for facilitating implantation of the apparatus 150 at an annulus of a heart valve. Each of the outer sheath 174 and the implantation flange 176 may be formed of any suitable flexible, biocompatible material, such as a cloth-like or fabric (natural or synthetic) material, a biological material, such as collagen or an animal tissue material. An acceptable animal tissue material is smooth animal pericardium (e.g., equine, bovine, porcine, etc.), such as a NO-REACT® tissue product.

FIGS. 7 and 8 illustrate a heart valve repair apparatus 200 in accordance with another aspect of the present invention. The apparatus 200 includes a generally annular base portion 202. The base portion 202 includes a support ring 203 that is dimensioned and configured to approximate the dimensions and configuration of a heart valve annulus, such as a mitral or atrioventricular valve. The support ring 203 may be substantially similar to that disclosed with respect to the base portions shown and described with respect to FIGS. 1–6 (e.g., it may be a complete ring (as shown) or a generally C-shaped ring).

A pair of support posts 204 and 206 extend generally axially from an outflow side 208 of the base portion 202. The supports 204 and 206 are circumferentially spaced apart from each other an arc length that approximates the circumferential dimension of a valve leaflet for which the apparatus 200 is intended to function. The support posts 204 and 206 may be formed of the same material or a different material as that which forms the base portion 202. For example, the support posts 204 and 206 and the base portion 202 may be formed as an integral unit in a suitable injection molding process. It is to be appreciated, however, that different materials also may be utilized to form the supports 204 and 206 and the base portion 202, with the supports being appropriately secured to the base portion, such as by ultrasonic welding or another method of attachment.

The apparatus 200 also includes a buttress 210 of a substantially flexible material that extends generally axially from the base portion 202 for providing a flexible surface for abutment with an adjacent leaflet of a heart valve. The buttress 210, for example, includes a flexible sheet 212 of material that is attached to the base portion 202 along a circumferentially extending arc 214 between the juncture of each of the support posts 204 and 206 and the base portion. The flexible sheet 212 of material extends generally axially from the base portion 202 and is connected to and extends between the support posts 204 and 206. The support posts 204 and 206 may be linear or curved to orient the sheath of flexible material connected therebetween at a desired position for engaging an adjacent leaflet. The sheet 212 of flexible material also may cover each of the support posts 204 and 206 as well as the annular base portion 202 so as to completely cover the frame, which is formed of the base portion and support posts. The sheet 212 of flexible material of the buttress 210 provides a radially inner surface 216 with which an adjacent leaflet may move into and out of engagement when the apparatus 200 is implanted. The flexible sheath 212 of material also may permit flexible movement of the buttress 210 relative to the supports 204 and 206, such that when the apparatus is implanted it facilitates coaptation between an adjacent leaflet (or leaflets) and the buttress.

As mentioned above with respect to the apparatus of FIGS. 1–4, the posts 204 and 206 and/or the base portion 202 may be formed of an inelastically deformable material. A surgeon implanting the apparatus 200, thus, may bend the buttress 210 and/or base portion 202 to a desired configuration. As a result, each apparatus may be customized for a patient so as to improve the operation of a heart valve when the apparatus 200 is implanted at the valve annulus.

The sheet 212 of flexible material, for example, may be a cloth or fabric material (natural or synthetic), a biological material, such as a sheet of collagen material or an animal tissue material, such as animal pericardium. In order to inhibit regurgitation of blood when implanted at a heart valve, the flexible sheath 212 of material should be substantially impervious to the flow of blood therethrough.

As illustrated in FIGS. 7 and 8, the apparatus also may include an implantation flange (or sewing ring) 220 for facilitating implantation of the apparatus at an annulus of a heart valve. The implantation flange 220 extends radially outwardly from the base portion 202. The implantation flange 220 is formed of a flexible material, such a cloth-like or fabric material (natural or synthetic), or a biological material, such as collagen or an animal tissue material. For example, the implantation flange 220 is formed of a biocompatible biological material, such as animal tissue (e.g., animal pericardium), which is the same material that forms the outer sheath 212.

FIG. 9 illustrates a frame 250 that may be employed to form an apparatus for helping repair a heart valve in accordance with another aspect of the present invention. For example, the frame 250 may be used to form an apparatus of a type similar to that shown and described with respect to FIGS. 1–4. The frame 250 provides a skeleton over which an outer sheath of a substantially flexible material may be applied.

The frame 250 includes a generally annular base portion 252. While the base portion 252 is illustrated as a complete ring, it will be understood and appreciated by those skilled in the art that an incomplete ring (e.g., a C-shaped ring) alternatively may be utilized in accordance with an aspect of the present invention. The base portion 252 includes an inflow side 254, and outflow side 256, with a central axis 258 extending through the base portion.

The frame 250 also includes a support 260 extending generally axially from the base portion 252. The axially extending support 260 is in the form of a curved structure that connects substantially opposed edges 262 and 264 of the base portion 252 for providing a support structure for a buttress.

The frame 250, for example, may be formed of a resilient material, a flexible material, or an inelastically deformable material, such as a plastic, a metal, or other material suitable for implantation into a human. The rigidity or flexibility of a material utilized to form the frame 250 may vary depending upon the amount of support desired at the annulus (by the base portion) as well as the amount of flexibility desired during coaptation between a leaflet and the buttress. The base portion 252 and the axially extending support 260 may be formed of the same or different materials, depending on the material properties (elasticity, rigidity, resilience, etc.) desired for each part of the frame 250.

The frame 250 may be covered with a sheet of a substantially flexible material to form an apparatus, similar to that shown and described with respect to FIGS. 1–4. A sheet of flexible material is applied over the frame so that the flexible material may be moveable relative to the axially extending support 260, such as in response to an adjacent leaflet moving into engagement with the overlying sheet of material. In contrast, the illustrated apparatus of FIGS. 1–4 employs a frame that includes a substrate material coextensive with the buttress onto which the sheet of flexible material is applied (e.g., the buttress of FIGS. 1–4 may be more static than the flexible buttress of FIG. 9).

FIG. 10 illustrates a heart valve repair apparatus 280 in accordance with another aspect of the present invention. Similar to the apparatus 10 of FIG. 1, the apparatus 280 includes a generally annular base portion 282 that is dimensioned and configured according to the dimensions and configuration of a heart valve annulus to which the apparatus is to be attached. As mentioned above with respect to FIGS. 1–4, the flexibility or resilience or rigidity of the base portion 282 may vary according to the material used to form the base portion, such as to provide a desired amount of support at the heart valve annulus.

A buttress 284 is attached to and extends radially inwardly and generally axially away from a posterior arc 286 of the base portion 282. More specifically, a proximal portion 288 of the buttress 284 extends axially and radially inwardly over a first portion of its length. A remaining portion 290 of the buttress 284 extends distally from the proximal portion 288 and curves radially outwardly relative to (or away from) the proximal portion. When the apparatus 280 is implanted, the buttress 284 provides a surface with which an adjacent leaflet may move into and out of engagement.

The apparatus 280 may be formed of a flexible and/or resilient material, such as a polymer or plastic-like material (e.g., Delrin®, pyrolythic carbon, etc.), a metal, or other material considered appropriate for implantation into a heart. The base portion 282 and the buttress 284, for example, may be formed of the same material to form an integral apparatus. Alternatively, different materials may be utilized to form each of the buttress 284 and the base portion 282, such as when different amounts of rigidity or flexibility may be desired for each respective part.

It will be understood and appreciated that the apparatus 280 further may be employed as the underlying frame 32 of the apparatus 10, as shown and described with respect to FIGS. 1–4. In order to form the apparatus 10 from the apparatus 280, an outer sheath of an appropriate flexible, biocompatible material is mounted over the apparatus 280, such as set forth above.

FIGS. 11 and 12 illustrate part of a heart 300 in which an apparatus, such as the apparatus 10 illustrated with respect to FIGS. 1–4, is implanted at an annulus 302 of a mitral valve 303. The mitral valve 303 is intended to provide for the unidirectional flow of blood from the left atrium 304 into the left ventricle 306. The mitral valve 303 includes an anterior leaflet 308 that extends from the annulus 300 adjacent the aortic opening 310 and attaches to the muscular tissue in the wall of the left ventricle by fibrous cordae tendinae 312. The posterior leaflet has been substantially removed from the heart, such as by excising it prior to implantation of the apparatus 10. It is to be understood and appreciated, however, that the posterior leaflet may remain intact, with a buttress 20 of the apparatus 10 interposed between the posterior and anterior leaflets.

As mentioned above, the apparatus 10 may include an implantation flange 36 that is sutured to the fibrous tissue at the annulus 302 of the valve 303. The buttress 20 extends from the base 12 of the apparatus 10 into the ventricle 306 at a position corresponding to the position of the posterior leaflet of the mitral valve 303. As mentioned above, the buttress 20 extends into the ventricle 306.

It is to be appreciated that the buttress 20 may be formed of a generally rigid material that remains substantially stationary (e.g., static) during both systole and diastole. Alternatively, the buttress 20 may be a sufficiently flexible material, such as a sheet of material supported in a peripheral frame (see, e.g., FIGS. 7–9) or by employing a more flexible type of frame to permit movement thereof commensurate with the flow of blood from the atrium 304 into the ventricle 306 through the valve 303.

FIG. 11 illustrates the mitral valve 303 is in a closed position (at systole), in which the anterior leaflet 304 engages the buttress 20 of the apparatus 10 in accordance with an aspect of the present invention. That is, the buttress 20 of the apparatus 10 simulates the function of the posterior leaflet at systole by providing a surface against which the anterior leaflet 308 coapts. As a result, the buttress 20 and the anterior leaflet 304 cooperate to inhibit regurgitation of blood from the left ventricle 308 into the left atrium 306, such as during ventricular contraction at systole.

The buttress 20 in conjunction with the anterior leaflet also facilitates and promotes unidirectional flow of blood at diastole, such as shown in FIG. 12 by arrow 314. In particular, an opening or aperture extends through the implanted apparatus 10 between the buttress 20 and the anterior leaflet 308. Advantageously, the movement of the anterior leaflet 308 relative to the buttress 20, in response to the flow of blood during diastole, provides a sufficient orifice to permit the free flow of blood from the left atrium 304 into the left ventricle 306. The buttress 20 also may be formed of a flexible material that is able to move radially relative to the base portion 12 to further facilitate blood flow. The annular base portion 12 of the apparatus 10 also may help support the annulus 302 of the mitral valve 303 at systole to promote the desired coaptation between the buttress 20 and the anterior leaflet 308 (FIG. 10).

As mentioned above, to reduce the invasiveness of the implantation procedure, the prosthesis can be configured to provide a variable cross-sectional dimension in accordance with an aspect of the present invention. That is, the prosthesis can be manipulated to a reduced cross-sectional dimension and placed within an enclosure of an implanter. The enclosure can be placed at a desired position (e.g., an annulus of a heart valve) within the patient's heart and the prosthesis ejected from the enclosure, so that the prosthesis expands to an expanded cross-sectional condition. In its expanded condition, at least the base portion engages surrounding tissue to help maintain a desired relative position within the heart. FIGS. 13–28 depict examples of prostheses, implantation devices and methods that can be used to provide for less invasive implantation of a prosthesis according to one or more aspects of the present invention.

Figure 13:
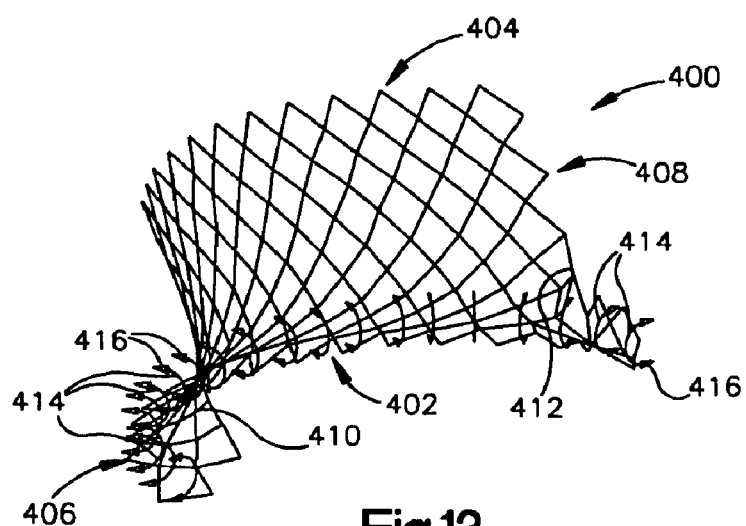
FIG. 13 is an isometric view of an example of a support frame having a variable cross-sectional dimension according to an aspect of the present invention.

FIG. 13 is an example of a support frame 400 that can be used to form a prosthesis to help improve operation of a patient's heart valve in accordance with an aspect of the present invention. The frame 400 includes an inflow end 402 and an outflow end 404. The frame 400 is dimensioned and configured to provide a desired contour for the prosthesis. In this example, the frame 400 includes a generally C-shaped base portion 406 at the inflow end 402. A buttress support portion 408 extends radially inwardly and axially from the base portion 406. The buttress support portion 408 can also turn radially outward at a distal portion near the outflow end 404.

According to an aspect of the present invention, the support frame can be deformable between reduced and expanded cross-sectional conditions. To provide the desired variability of the cross-sectional dimension in the example of FIG. 13, the frame 400 is formed of a wire or filament configured as a mesh or weave extending between the ends 402 and 404. The mesh may be a metal, an alloy, or other suitable material that will endeavor to maintain its configuration and, in turn, help anchor the prosthesis at a desired position when implanted. To obtain a reduced cross-sectional dimension for the frame (and a prosthesis that includes the frame), the frame can be rolled between ends 410 and 412 inwardly along its C-shaped circumference or be compressed by applying a radially inward external force.

By way of example, the mesh may be formed of a shape memory alloy material, such as a nitinol (nickel-titanium alloy) wire. Shape memory (or thermal memory) is a characteristic in which a deformed part remembers and recovers to a pre-deformed shape upon heating. By forming the frame 400 of a shape memory alloy, the frame is inelastically deformable to new shape, such as to a reduced cross-sectional dimension, when in its low-temperature (martensitic) form. For example, the frame can be cooled, such as by being introduced to a cooling solution (e.g., water), and then compressed to its reduced cross-sectional condition.

When the frame 400 is heated to its transformation temperature, which may vary according to the alloy composition, it reverts to its high-temperature (austenitic) form. A prosthesis that includes the frame 400 thus may retain the compressed condition by keeping it cooled. Alternatively, the frame may be retained in the compressed position, such as with sutures or other retaining features circumscribing the structure, a cylindrical enclosure around the structure, etc. The frame 400 and associated prosthesis will then return toward its high-temperature (or original) position upon removal of the retaining element.

It is to be appreciated that, alternatively, a frame, in accordance with an aspect of the present invention, could be inelastically deformable so as to require an intervening force or a stimulus (e.g., other than temperature) to return the deformed frame to a desired expanded configuration. For example, a balloon catheter, spring mechanism or electrical current could be employed to urge the frame and prosthesis to its expanded condition so that, after being implanted at a desired position, the frame will engage the surrounding tissue in a manner to inhibit movement relative to the surrounding tissue. Alternatively, the frame can be a resilient material that seeks to return to its original expanded state.

The frame 400 also can include spikes (or protrusions) 414 extending generally radially outwardly from the base 406. The spikes 414 can be formed as one or more rows spaced axially apart. In the example of FIG. 13, the spikes 414 are formed of small C-shaped members, the ends of which terminate in barbs or other features 416 to help grip surrounding tissue when implanted. The ends of each C-shaped spike members can be axially displaced, as shown in FIG. 13, or they could be oriented in other relationships, which could be the same or different relationships circumferentially along the base 406.

Figure 14:
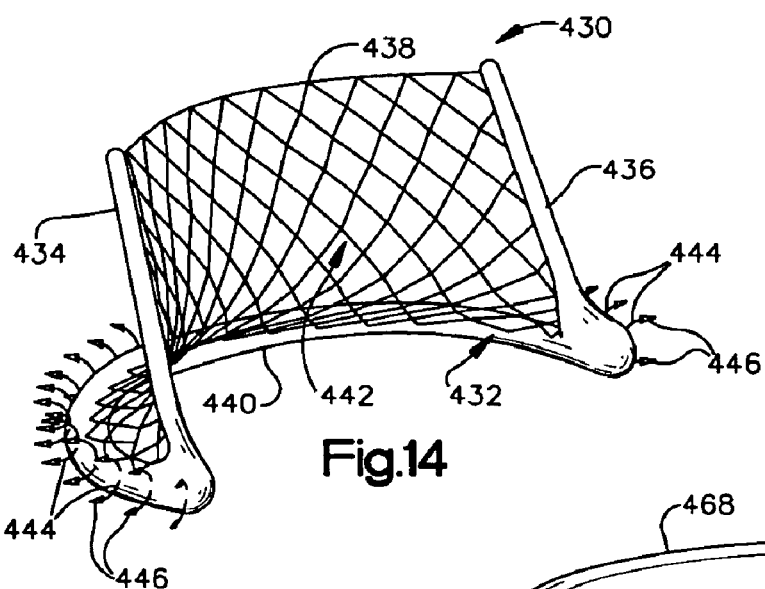
FIG. 14 is an isometric view of an example of a support frame having a variable cross-sectional dimension according to an aspect of the present invention.

FIG. 14 depicts another example of a frame 430 that can be utilized to form a prosthesis in accordance with an aspect of the present invention. In this example, the frame 430 includes a generally C-shaped base portion 432, such as can be formed of a material (e.g., metal wire, a shape memory alloy, plastic or other material) that is compressible to a reduced cross-sectional dimension and expandable to an expanded cross-sectional dimension. Posts 434 and 436 extend generally axially from the base at opposed ends of the C-shaped member and terminate near an outflow end 438 of the frame 430. The base portion 432 defines the inflow end of the frame. The posts 434 and 436 can be formed of the same material as the base, such as to form an integrated frame. Alternatively, the posts 434 and 436 can be formed of different materials from the base and can be attached to the base 432 by any suitable fastening means.

The frame 430 also includes a web 442 of material that extends between the posts and the base portion 432. The extent of the web 442 between distal ends of the posts 434 and 436 defines another part of the outflow end 438. The web 442 of material, which can be metal, plastic, or other natural or synthetic materials, is configured to provide a desired contour for a buttress portion of the prosthesis. The web 442 extends radially inwardly and axially from the base portion 432 to define a buttress or support. Additionally, the web 442 is formed of a material that facilitates reduction and expansion of the frame 430 between reduced and expanded cross-sectional conditions in accordance with an aspect of the present invention. In the illustrated example, the web 442 is in the form of a mesh material, such as a biocompatible metal wire, which can be woven by one or more lengths of an appropriate wire. The web 442 also provides a desired resilient support in the expanded condition. The frame parts for the base portion 432 and the buttress 442 can be formed of the same or different materials depending on the material properties (elasticity, rigidity, resilience, etc.) desired for each part of the frame 400. Different thicknesses of the same or different materials can also be utilized to achieve desired tensile properties.

The frame 430 can also include a plurality of spikes 444 extending generally radially outwardly from the base portion 432, such as shown and described with respect to FIG. 13. The spikes 444 can be formed as one or more rows spaced axially apart, such as the generally C-shaped members having barbed ends 446 to help grip surrounding tissue when implanted.

Figure 15:
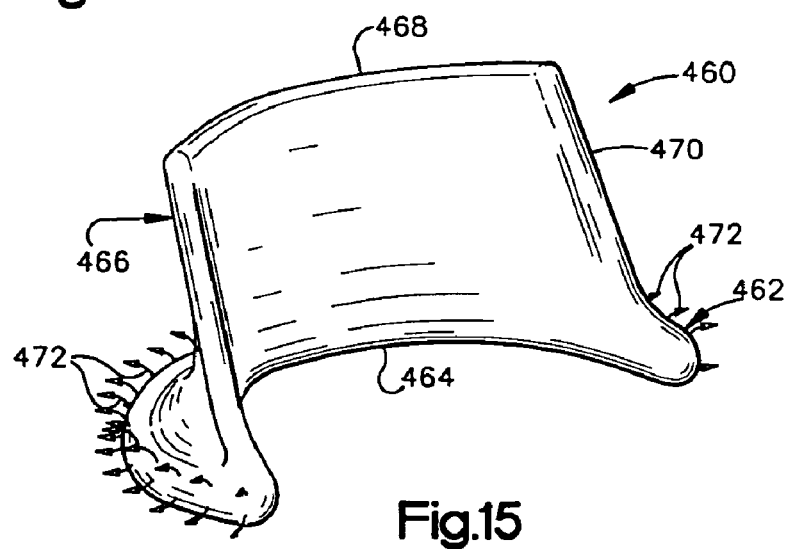
FIG. 15 is an isometric view of an example of an apparatus in accordance with another aspect of the present invention.

FIG. 15 illustrates an example of a prosthesis 460 that can be formed from a frame, such as the frames 400 or 430 shown and described in FIGS. 13 and 14, respectively. The prosthesis 460 thus includes a generally C-shaped base portion 462 at an inflow end 464 and a buttress or support 466 extending axially and radially inwardly from the base to terminate in an outflow end 468.

As mentioned above, the support frame can be sufficiently flexible and resilient to permit the prosthesis 460 to be compressible to a reduced cross-sectional dimension during positioning and then expand (e.g., automatically or upon being stimulated) to an increased cross-sectional dimension. For example, the apparatus 460 can be located within a barrel of an implantation device. For example, the barrel can form part of a catheter for implantation through a vessel or another type implantation system, which can be utilized to implant the apparatus under direct or hidden (e.g., video assisted) vision of the surgeon.

In accordance with an aspect of the present invention, an outer sheath 470 of a biocompatible material covers at least a substantial portion of the underlying frame (see FIGS. 13 and 14). The outer sheath 470 can be formed of one or more sheets of a biocompatible material that are applied over the frame. In one particular aspect, the outer sheath 470 can completely cover the entire frame, including the base portion and the buttress extending therefrom.

The outer sheath 470 may be substantially any material, such as a cloth-like or fabric material (natural or synthetic), a biological material, such as collagen or an animal tissue material. An acceptable animal tissue material is smooth animal pericardium (e.g., equine, bovine, porcine, etc.) that has been tanned or fixed in a suitable tanning environment.

By way of further example, the outer sheath 470 can be pericardium (or other biological material) that has been cross-linked with glutaraldehyde and has undergone a detoxification process with heparin bonding, such as one of the NO-REACT® natural tissue products that are commercially available from Shelhigh, Inc. of Millburn, N.J. The NO-REACT® natural tissue products exhibit improved biocompatibility and mitigate calcification and thrombus formation. The exposed smooth animal pericardium covering the buttress 20 further inhibits abrasion that could occur in response to engagement between a leaflet and the buttress when implanted in accordance with an aspect of the present invention.

Spikes 472, which extend from the frame, further protrude through the outer sheath 470 such as along a perimeter of the base portion. The spikes 472 help maintain the prosthesis at a desired position when implanted. Different portions of the spikes can be provided in different lengths in order to mitigate damage to surrounding tissue. For example, a portion of the spikes, such as near opposed ends of the C-shaped base portion, can be shorter than those opposite the space between the ends of the C-shaped base. In this way the shorter spikes can be aligned and inserted a lesser amount into the surrounding tissue yet still help maintain a desired position for the prosthesis. Longer spikes can be aligned and inserted into tissue that can better accommodate longer spikes.

Those skilled in the art will understand and appreciate various changes that can be provided to adjust the contour or rigidity (or flexibility) of the prosthesis 460. For example, if additional support is desired, one or more other support members (not shown) can connect the base portion 462 and a radially outer extent of the buttress portion 466 (e.g., on a side of the buttress opposite of where the ends of the C-shaped base portion are located. Additional spikes or protrusions can extend from the added support member(s) or from a posterior side of the buttress (not shown) to further help hold the implanted prosthesis at a desired location when implanted.

Figure 18:
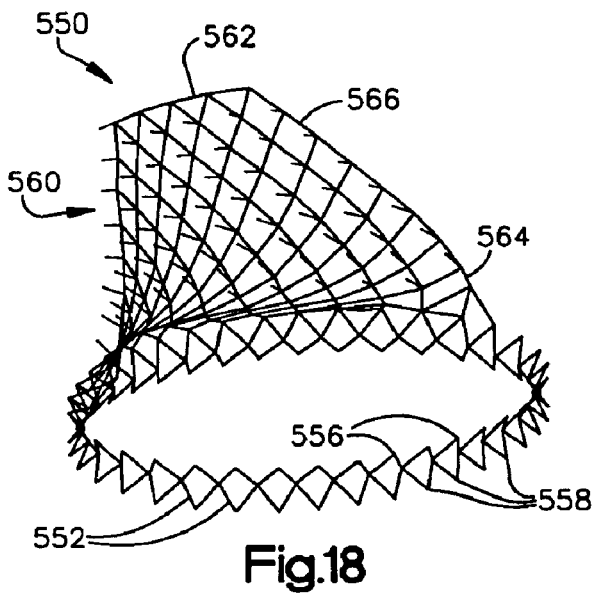
FIG. 18 is an isometric view of another example of a support frame having a variable cross-sectional dimension according to an aspect of the present invention.
Figure 19:
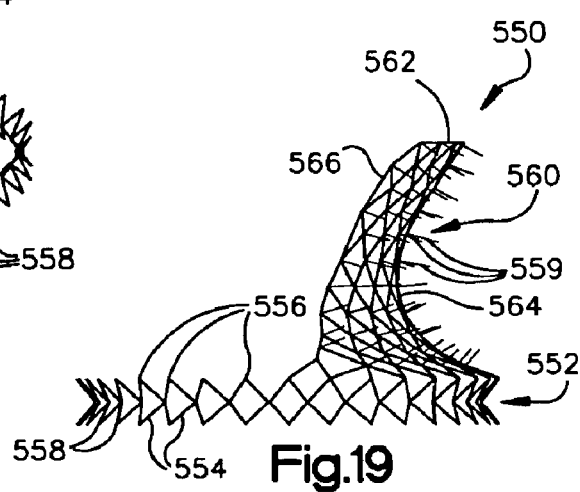
FIG. 19 is side view of the support frame of FIG. 18.
Figure 20:
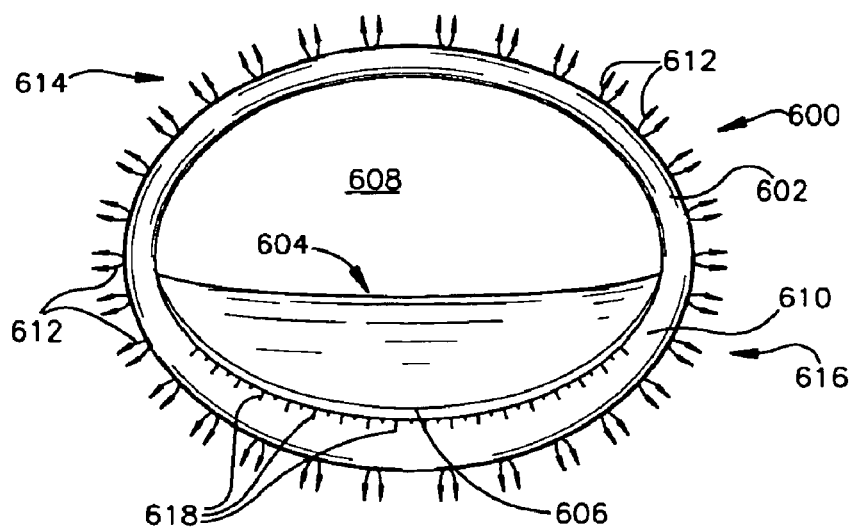
FIG. 20 is an outflow view of an apparatus in accordance with another aspect of the present invention.

FIGS. 16, 17, 18 and 19 illustrate two alternative types of frames that can be utilized to make a prosthesis for helping improve operation of a heart valve, such as shown in FIG. 20, in accordance with an aspect of the present invention. The frames are generally similar to that shown and described in FIGS. 13 and 14, except that the base portion is annular instead of the C-shaped.

Figure 16:
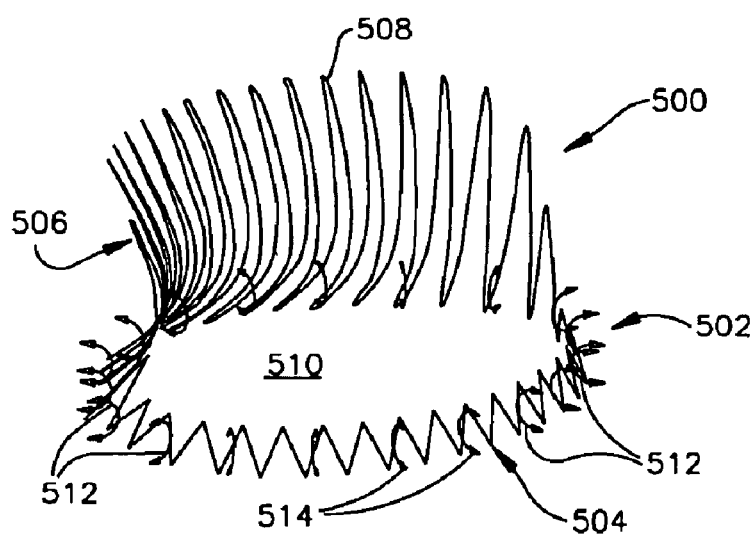
FIG. 16 is an isometric view of an example of a support frame having a variable cross-sectional dimension according to an aspect of the present invention.

With reference to FIG. 16, a frame 500 is illustrated that can be employed to form a prosthesis to help improve operation of a patient's heart valve in accordance with an aspect of the present invention. The frame 500 includes a generally annular base portion 502 at an inflow end 504. A buttress support portion 506 extends radially inwardly and axially from the base portion 502 to terminate in an outflow end 508 spaced apart from the base portion. The buttress support portion 506 can also turn radially outward at a distal portion near the outflow end 508. An aperture 510 extends through the base portion 502 of the frame 500.

According to an aspect of the present invention, the support frame 500 can be deformable between reduced and expanded cross-sectional conditions. To provide the desired variability of the cross-sectional dimension in the example of FIG. 16, the frame 500 is formed of a zig-zag (or generally sinusoidal) wire mesh or weave extending between the ends 504 and 508, in which the space between adjacent zig-zags (or sinusoids) is determined by the cross-sectional dimension of the frame. The circumferential distance between adjacent zig-zags (or sinusoids) can also be lessened at desired areas in which a greater rigidity is desired, such as at or near lateral edges of the buttress portion 506. To provide further support for the buttress portion 506, one or more other support structures (not shown) can connect the base portion 502 and a radially outer extent of the buttress portion 506 (e.g., on a side of the buttress opposite of where the aperture 510 is located).

By way of example, the material that forms the frame 500 may be a metal, an alloy, or other suitable material that will endeavor to maintain its configuration and, in turn, help anchor the prosthesis at a desired position when implanted, such as described herein. To obtain a reduced cross-sectional dimension for the frame 500 (and a prosthesis that includes the frame), the frame can be compressed, such as by applying a radially inward force generally along its circumference.

To help maintain the position of a prosthesis incorporating the frame 500 when implanted, the frame can include a plurality of spikes or other protruding features 512 that extend generally radially outwardly from the base portion 502. As mentioned above, the spikes 512 can be formed as one or more rows of spikes spaced axially apart, such as generally C-shaped members, having barbed ends 514 to help grip surrounding tissue when implanted. Alternatively, inflow and outflow ends of the base can be turned outwardly to define the spikes.

Figure 17:
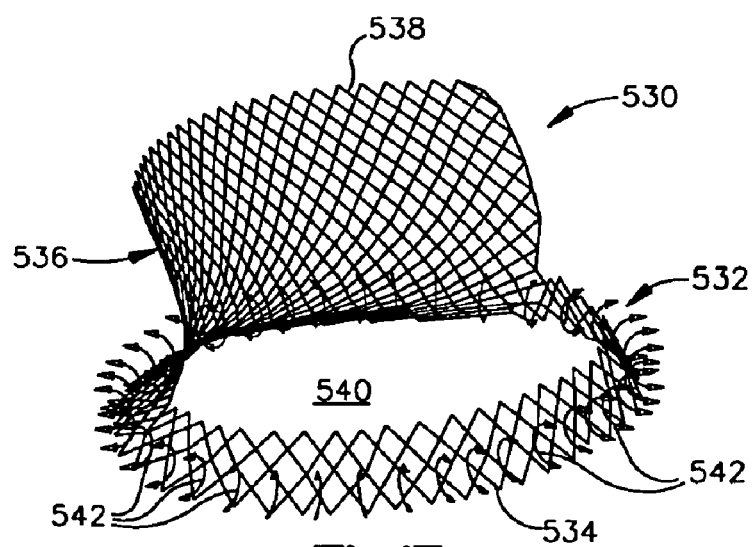
FIG. 17 is an isometric view of an example of a support frame having a variable cross-sectional dimension according to an aspect of the present invention.

FIG. 17 depicts another example of an annular frame 530 that can be utilized to form a prosthesis to help improve operation of the heart valve in accordance with an aspect of the present invention. The frame 530 is similar to that shown and described in FIG. 16, although a more dense mesh is employed to form the frame. Briefly stated, the frame 530 includes an annular base portion 532 associated with an inflow end 534 and a buttress support portion 536 that extends from the base portion to provide an outflow end 538 axially spaced from the inflow end. The buttress support portion 536 extends radially inwardly and axially from the base portion 534. The buttress support portion 536 can also turn radially outward at a distal portion near the outflow end 508. An aperture 540 extends through the base portion 502 of the frame 500.

A plurality of protruding features or spikes 542 can extend from the base portion to facilitate its ability to grip surrounding tissue when implanted. An noted above, the spikes 542 can be in the form of generally C-shaped wire members having barbed ends that extend outwardly from the base portion 532 to facilitate the gripping of adjacent tissue when implanted. The spikes 542 can be provided along some or the entire circumference of the base portion 532. The spikes 542 can also be provided in different lengths to provide different levels of attachment to surrounding tissue.

FIGS. 18 and 19 illustrate another example of a frame 550 that can be utilized as part of a prosthesis for helping improve operation of a heart valve in accordance with an aspect of the present invention. The frame 550 includes an annular base portion 552 configured to facilitate changing between an expanded cross-sectional dimension (as shown in FIG. 18) and a reduced cross-sectional dimension (as shown in FIG. 19). In this example, the base portion 552 appears a plurality of diamond-shaped members 554 of a mesh or weave that are interconnected at lateral edges thereof to form a mesh. The members 554 can be formed form one or more wires that are interwoven to form the base portion 552. In order to facilitate gripping to surrounding tissue when implanted, axially opposed ends 556 and 558 of at least some and suitable all of the members 554 can protrude radially outwardly relative to a central part of the respective members to define spikes. Thus, the side edges of the base portion 552 appear as a C-shaped end and an inverted C-shaped end. An additional set of one or more spikes or protrusions 559 can be provided at a posterior side of the buttress. By way of example, the posterior spikes 559 can engage and/or penetrate a damaged or defective leaflet (e.g., a posterior leaflet when implanted at an annulus of a mitral valve) of a patient's valve and further help maintain a desired position relative to the valve.

The frame 550 also includes a buttress support portion 560 that extends from an arc along the base portion 552 and terminates in an outflow end 562. As shown in the side view of FIG. 19, a proximal part 564 of the buttress support 560 extends axially from the base and radially inwardly therefrom for a length. A distal part 566 of the buttress support portion 560 further extends axially and turns radially outwardly.

FIG. 20 is an example of a prosthesis 600 (as seen from is outflow end) that can be provided to help improve operation of a heart valve in accordance with an aspect of the present invention. The prosthesis 600 illustrates an example of a prosthesis 460 that can be formed from a frame, such as the frames 500, 530 or 550 shown and described in FIGS. 16–19 respectively. The prosthesis 600 thus includes a generally annular base portion 602 at an inflow end of the prosthesis and a buttress or support 604 extending axially and radially inwardly from the base portion to terminate in an outflow end 606. The buttress 604 is provided along an arc length of the base portion and extends axially and radially inwardly for a proximal portion and then turns radially outwardly for a distal portion.

An aperture 608 extends through the prosthesis 600 between the base 602 and the buttress 604 to permit substantially bi-directional flow of fluid therethrough.

As mentioned above, the support frame can be sufficiently flexible and resilient to permit the prosthesis 600 to be manipulated to a reduced cross-sectional dimension (such as during positioning of the prosthesis) and then to expand (e.g., automatically or upon being stimulated) to an increased cross-sectional dimension. For example, the prosthesis 600 can be implanted within a barrel of an implantation device, such as a catheter for implantation through a vessel or another type of implantation system, which can be utilized to implant the prosthesis under direct or hidden (e.g., video assisted) vision of the surgeon.

In accordance with an aspect of the present invention, an outer sheath 610 of a biocompatible material covers at least a substantial portion of the underlying frame (see FIGS. 16–19). The outer sheath 610 can be formed of one or more sheets of a biocompatible material that are applied over the frame. In one particular aspect, the outer sheath 610 can completely cover the entire frame, including the base portion and the buttress support frame.

The outer sheath 610 may be substantially any material, such as a cloth-like or fabric material (natural or synthetic), a biological material, such as collagen or an animal tissue material. An acceptable animal tissue material is smooth animal pericardium (e.g., equine, bovine, porcine, etc.) that has been tanned or fixed in a suitable tanning environment. By way of further example, the outer sheath 610 can be formed of one or more sheets of a biological material that has been cross-linked with glutaraldehyde and has undergone a detoxification process with heparin bonding, such as one of the NO-REACT® tissue products available from Shelhigh, Inc. of Millburn, N.J.

Spikes 612, which extend from the frame, further protrude through the outer sheath 610 such as along a perimeter of the base portion. The spikes 612 help maintain the prosthesis 600 such as along a perimeter of the base portion. The spikes 612 help maintain the prosthesis 600 at a desired position when implanted. Different portions of the spikes 612 can be provided in different lengths in order to mitigate damage to surrounding tissue. For example, a portion of the spikes, indicated at 614, can be shorter than those spikes, indicated at 616, that protrude from the base near where the buttress 604 extends from the base 602. In this way the shorter spikes 614 can be aligned and inserted a lesser amount into the surrounding tissue yet still help maintain a desired position for the prosthesis. Longer spikes 616 can be aligned and inserted into tissue that can better accommodate longer spikes, thereby providing for more secure attachment of the implanted prosthesis 600. While the spikes in the example of FIG. 20 are depicted as being provided in pairs (e.g., corresponding to the C-shaped spike members of FIGS. 16 and 17), other configurations of spikes (e.g., the triangular end portions along the base 556 and 558 of FIGS. 18 and 19) also could be utilized in accordance with an aspect of the present invention.

An additional set of spikes 618 also can protrude from the posterior side of the buttress. These additional spikes 618 can engage and/or penetrate a damaged or defective leaflet of a heart valve at which the prosthesis 600 is implanted, thus further helping maintain the position of the implanted prosthesis.

Those skilled in the art will understand and appreciate various changes that can be provided to adjust the contour or rigidity (or flexibility) of the prosthesis 600. For example, if additional support is desired, one or more other support members (not shown) can connect the base portion 602 and a radially outer extent of the buttress portion 604 (e.g., on a side of the buttress opposite of where the ends of the C-shaped base portion are located.

Figure 21:
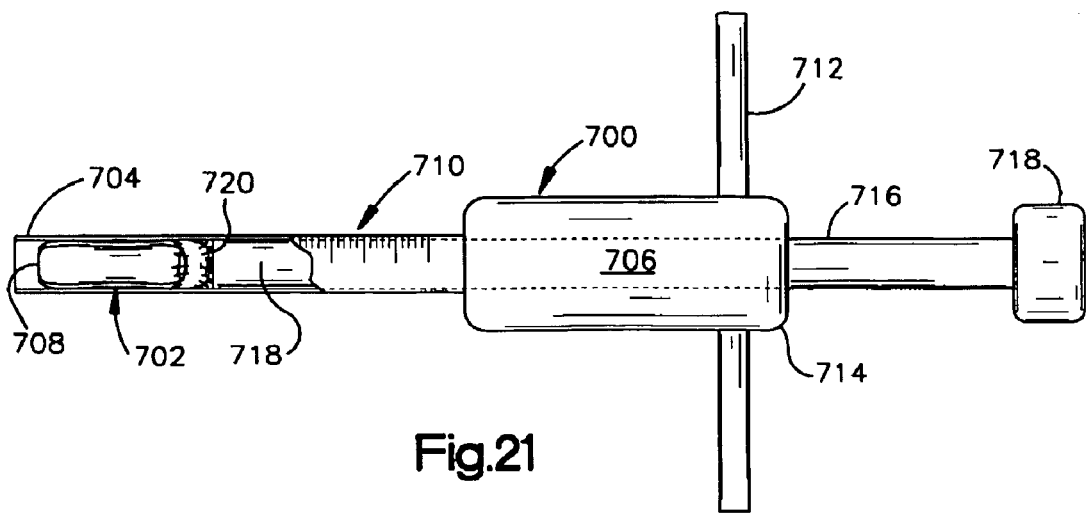
FIG. 21 is an example of an implanter apparatus for implanting a prosthesis in accordance with an aspect of the present invention.

FIG. 21 illustrates an implanter apparatus 700 for implanting a prosthesis 702 in accordance with an aspect of the present invention, such as to facilitate sutureless implantation of the prosthesis. The implanter 700 includes an elongated cylindrical barrel 704 that extends from a body portion 706 and terminates in an open end 708. The barrel 704 has an inner diameter that is less than the outer diameter of the prosthesis 702 in its expanded condition. Thus, in order to insert the prosthesis 702 into the barrel 704, the prosthesis must be deformed to a reduced cross-sectional dimension, such as at about one-half or less of its fully expanded condition.

For example, the inner diameter of the barrel 704 can range from about 5 mm to about 15 mm, whereas the outer diameter of the prosthesis 702 (in its expanded condition) typically ranges from about 15 mm to about 40 mm. Thus, the barrel 704 can accommodate a prosthesis 702, which has been deformed to reduced cross-sectional dimension. The exterior of the barrel 704 further can include indicia (e.g., ruler markings) 710 that can help indicate the distance the barrel is inserted into a patient.

The implanter 700 also includes a handle 712 that extends outwardly from a proximal end 714 of the body portion 706. The handle 712, which may be gripped by a surgeon, facilitates manipulating the barrel 704 along a desired path. A plunger 716 has a distal end 718 that can be urged into engagement with the prosthesis 702 to push the prosthesis from the opening 708 of the barrel 704. The plunger 716 includes an elongated portion that extends from its distal end 718 and terminates in a proximal end portion 718. The proximal end portion 718 operates as a trigger that can be grasped by a surgeon to move the plunger through the barrel 704. Other means to discharge the prosthesis 702 also could be utilized in accordance with an aspect of the present invention. Fluid, such as saline, also can be introduced into the barrel 704, such as through an opening (not shown) in the plunger 716, to facilitate the discharge of the prosthesis 702 from the barrel.

In the examples of FIG. 19 the prosthesis 702 is positioned within the barrel 704 with its inflow end 720 adjacent to plunger 718. Those skilled in the art will understand and appreciate that the outflow end 722 of the prosthesis 702 alternatively could be positioned adjacent the opening 708 of the barrel. The particular orientation of the prosthesis 702 (e.g., along its inflow and outflow ends) within the barrel 704 will depend on where the prosthesis is being implanted and the direction from which the implanter 700 is being inserted relative to the implant site. In accordance with a particular aspect of the present invention, the implanter 700 and prosthesis 702 is particularly useful for an open chest procedure in which the prosthesis is introduced into the heart under substantially direct vision of the surgeon.

For example, the implanter 700 could be introduced into a blood vessel (e.g., the pulmonary artery or aorta) that provides a substantially direct and linear path to the desired implantation position. Further, the procedure can be implemented without cardiopulmonary bypass, such as when the prosthesis is implanted through the pulmonary artery or directly through the patient's heart muscle (e.g., through the anterior wall of the patient's right ventricle). Alternatively, cardiopulmonary bypass can be used, but advantageously for a generally short period of time, such as when the prosthesis is implanted at the aortic position. Bypass generally is required when implanting at the aortic position due to the relatively high blood pressure as well as to facilitate decalcification of the patient's existing heart valve, if needed.

By way of further example, a low invasive minithoracotomy can be used to gain access to the heart of the patient and then inserting the barrel 704 of the implanter 700 through the passage. The surgeon can further be guided by an appropriate vision system to help guide the barrel 704 to a desired position for implanting the prosthesis 702, such as through a blood vessel or directly through the heart muscle. As noted above, it will further be appreciated that such a procedure can be implemented with little or no cardiopulmonary bypass.

Figure 22A:
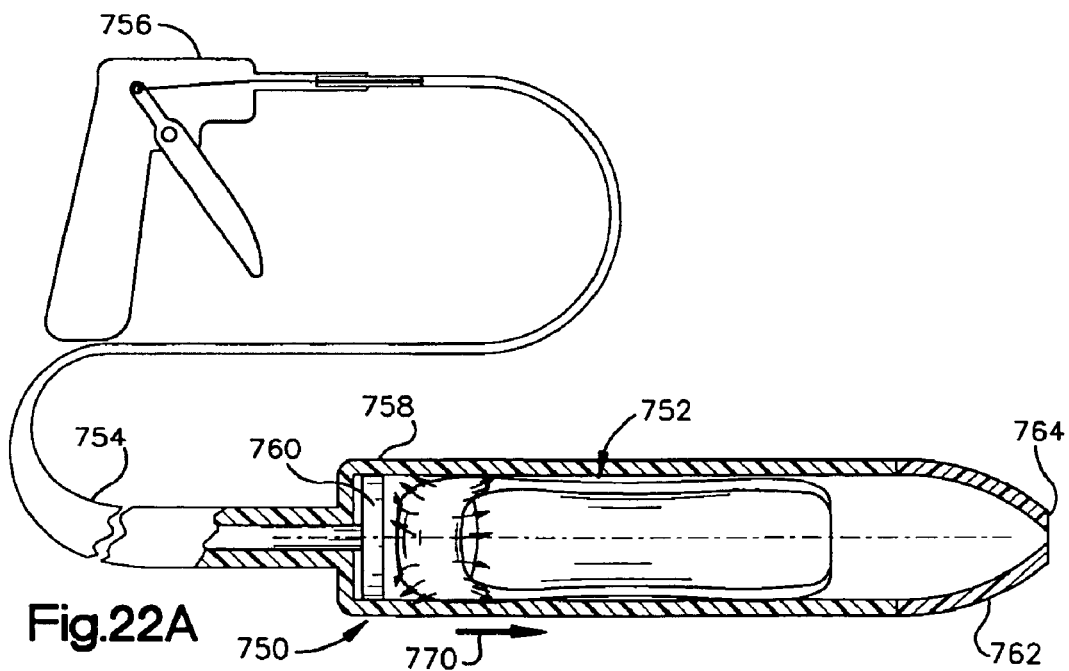
FIG. 22A is an example of a catheter mechanism that may be utilized for implanting a prosthesis in accordance with an aspect of the present invention.
Figure 22B:
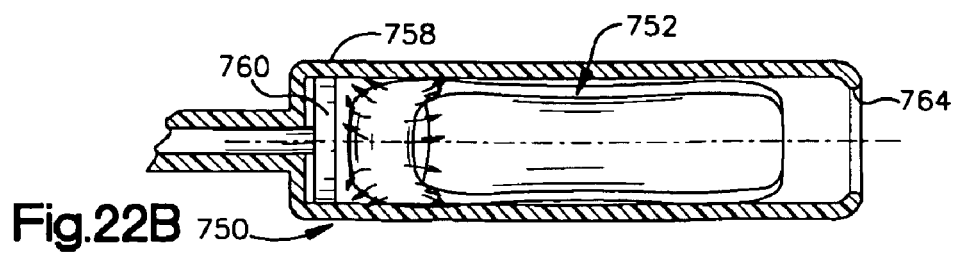
FIG. 22B is an example of another type of catheter mechanism that may be utilized for implanting a prosthesis in accordance with an aspect of the present invention.

FIGS. 22A and 22B illustrate variations of an implantation apparatus 750 that may be utilized to implant a prosthesis 752 in accordance with an aspect of the present invention. It is to be understood and appreciated that any of the prostheses shown and/or described herein can be implanted with such an implantation apparatus. For purposes of example, a prosthesis having a generally annular base portion is shown in FIGS. 22A and 22B.

With reference to FIG. 22A, by way of example, the implantation apparatus 750 may be in the form of a catheter system. The implantation apparatus includes an elongated connecting element 754 extending between a trigger mechanism 756 and an enclosure 758, in which the prosthesis 752 is located. At least a portion of the prosthesis 752 is located within the enclosure 758. A plunger mechanism 760 is located at a proximal end of the enclosure 758 for urging the prosthesis 752 generally axially from the enclosure 758. An opposite end 762 of the enclosure 758 may be formed of a pliable material or a plurality of moveable members that may open as the prosthesis 752 is urged through an opening 764 located at a distal end. It is to be appreciated that the length of the connecting element 754 may vary according to where the prosthesis 752 is to be implanted and the method of implantation. The barrel 758 also can be rotatable about its longitudinal axis to facilitate proper angular orientation of the prosthesis 752 during implantation at the patient's heart valve.

The prosthesis 752 is illustrated within the enclosure 758 as having its reduced cross-sectional condition, such as described herein. That is, the prosthesis 752 within the enclosure 758 has a cross-sectional dimension that is less than its normal (or expanded) cross-sectional dimension, being maintained in such position by the enclosure. Those skilled in the art will appreciate that the orientation of the inflow and outflow ends of the prosthesis 752 will vary depending upon the direction in which blood is to flow through the valve when implanted.

The compression of the prosthesis 752 and insertion into the barrel can be performed just prior to surgery. The plunger mechanism 760 may be urged in the direction of arrow 770, such as by activating the trigger 756. Movement of the plunger 760, in turn, causes the prosthesis 752 to also be moved in the direction of the arrow 770 within the barrel 758. As the prosthesis 752 is urged through the opening 764 and discharged therefrom, the prosthesis may expand, either automatically or upon a stimulus (e.g., temperature, electrical energy, or cutting a retaining element around the prosthesis). Accordingly, the opening 764 should be positioned at the location where the prosthesis 752 is to be implanted prior to being discharged. When the prosthesis 752 expands toward its expanded condition, the sidewall of the base portion and/or associated spikes may engage and/or penetrate into surrounding tissue so as to mitigate axial movement and rotation of the prosthesis relative to the surrounding tissue and the patient's valve at which the prosthesis is implanted. As a result, the prosthesis may be implanted without sutures to cooperate with the patient's valve (which can be the patient's original valve or a replacement valve) to provide a competent valve in accordance with an aspect of the present invention. The prosthesis can be implanted either as part of an open chest procedure or the patient's chest may be closed.

FIG. 22B illustrates another example of an alternative barrel 758 configuration which may be utilized, in accordance with an aspect of the present invention, to implant a prosthesis 752. The enclosure 758 has an opening 764 at its distal end through which the prosthesis 752 may be discharged. In this example, the opening 764 is about the same diameter as the enclosure itself, although it may be curved slightly inwardly at the distal end thereof. This facilitates discharge of the prosthesis 752 without having an expandable distal end portion, such as shown and described with respect to FIG. 22A.

Those skilled in the art will understand and appreciate that any of the prostheses shown and described herein can be implanted using any of the implantation devices, such as shown and described in FIGS. 21, 22A and 22B. It further is to be appreciated that other configurations of implantation devices could also be utilized to implant such prosthesis according to an aspect of the present invention.

Figure 23:
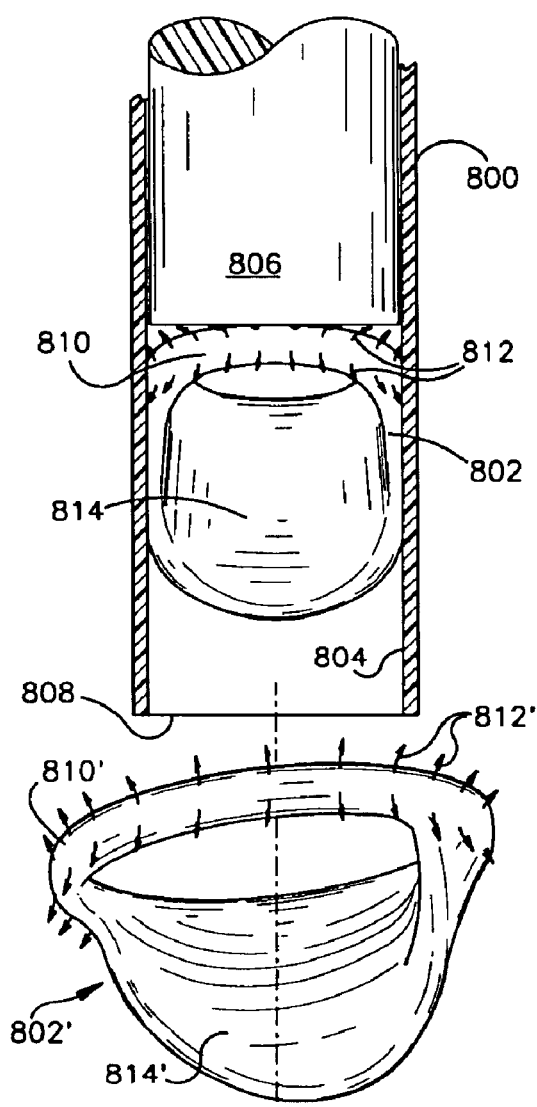
FIG. 23 is an example of a prosthesis within a barrel and discharged therefrom in an expanded cross-sectional dimension in accordance with an aspect of the present invention.
Figure 24:
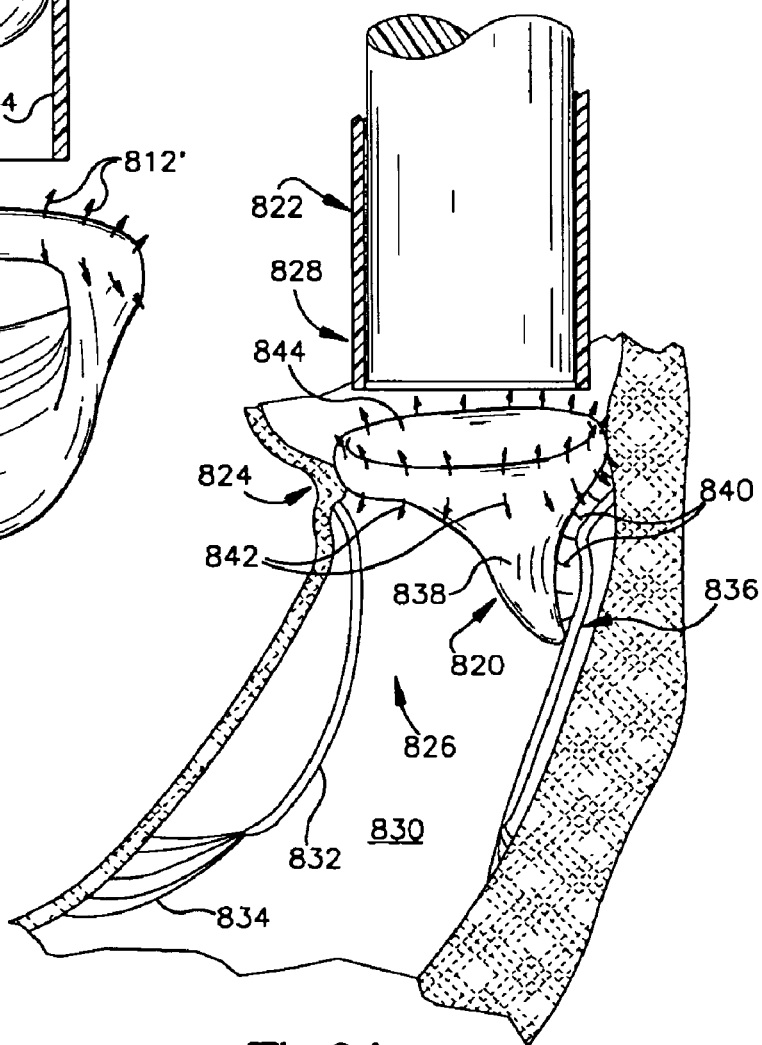
FIG. 24 is an example of a prosthesis implanted in an expanded condition to help improve operation of a patient's heart valve in accordance with an aspect of the present invention.

FIGS. 23 and 24 illustrate examples of using an implanter system in accordance with an aspect of the present invention. FIG. 23 illustrates a barrel 800 of an implanter in which a prosthesis 802 is located. The prosthesis 802 is maintained in a substantially reduced cross-sectional dimension within the barrel 800 due to its engagement with the interior sidewall 804 of the barrel. Within the barrel 800 is a plunger 806 that can be advanced toward a distal end 808 of the barrel to discharge the prosthesis 802. The prosthesis is shown in its expanded condition at 802' (a prime symbol indicates parts of the prosthesis in its expanded condition) below the barrel 800, such as after having been discharged from the barrel. The prosthesis 802, 802' is illustrated as a type having an annular base portion 810, 810' and a plurality of spikes 812, 812' protruding from the circumference of the base. The prosthesis 802, 802' also includes a buttress 814, 814' that extends from an arc of the base generally radially inwardly for a first axial part of the buttress and turns radially outwardly for a second axial part to terminate in an outflow end thereof.

FIG. 24 depicts a prosthesis 820 implanted from an implanter device 822 at an annulus 824 of a mitral valve 826 in accordance with an aspect of the present invention. The mitral valve 826 is intended to provide for the unidirectional flow of blood from the left atrium 828 into the left ventricle 830. The mitral valve 826 includes a functioning anterior leaflet 832 that extends from the annulus 824 adjacent the aortic opening and attaches to the muscular tissue in the wall of the left ventricle by fibrous cordae tendinae 834. The posterior leaflet 836 is located between a posterior side of a buttress 838 of the prosthesis 820. In the example of FIG. 24, it is assumed that the posterior leaflet is defective or damaged. Although, it will be understood and appreciated that the prosthesis alternatively could be used to help operation of a functioning posterior leaflet, such as if the anterior leaflet was damaged or defective.

Spikes 840 are illustrated extending from the posterior side of the buttress 838 and engaging and/or penetrating the posterior leaflet 836 or vessel wall, which helps maintain the prosthesis in a desired position and orientation relative to the patient's valve 826. The prosthesis 820 also includes other spikes 842 that protrude from a base portion 844 of the prosthesis for engaging and/or penetrating surrounding tissue at the annulus 824.

As mentioned above, the buttress 838 extends axially from an arc of the base portion 844 radially inwardly for a first part of its length and then curves radially outwardly for a second part of its length. Thus, at least a portion of the buttress 838 extends into the ventricle 830 generally. With such configuration, the anterior leaflet 832 can move into and out of engagement with the anterior surface of the leaflet, thereby controlling the flow of blood through the valve 826. As a result of cooperation between the leaflet 832 and the anterior surface of the buttress 838 unidirectional flow of blood can be provided through the valve 826 and the prosthesis 820 in accordance with an aspect of the present invention.

Figures 25, 26:
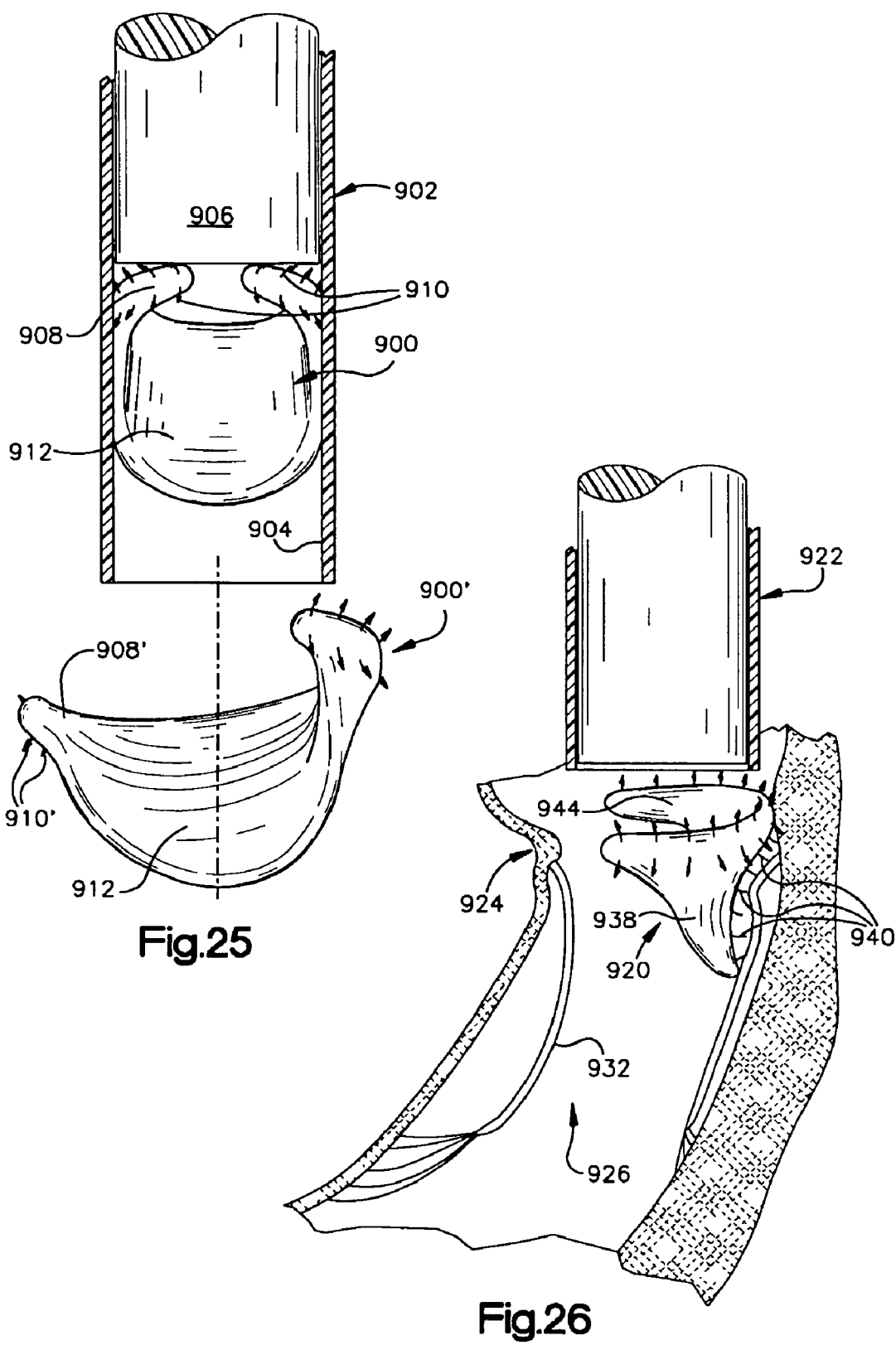
FIG. 25 is an example of a prosthesis having a reduced cross-sectional dimension within an barrel and discharged therefrom in an expanded cross-sectional dimension in accordance with an aspect of the present invention.
FIG. 26 is an example of a prosthesis implanted in an expanded condition to help improve operation of a patient's heart valve in accordance with an aspect of the present invention.

FIGS. 25 and 26 are views similar to FIGS. 23 and 24, but depict prostheses having C-shaped cross-sections. Briefly stated, FIG. 25 illustrates a prosthesis 900 located within a barrel 902 of an implanter. The prosthesis 900 is maintained in a substantially reduced cross-sectional condition corresponding to the dimensions of the interior sidewall 904 of the barrel 902. The implanter includes a plunger 906 that can be advanced to discharge the prosthesis 900 from the barrel 902.

The prosthesis 900 is shown in its expanded condition external to the barrel, as indicated at 900' (a prime symbol indicates parts of the prosthesis in its expanded condition), such as after having been discharged from the barrel 902. The prosthesis 900, 900' is illustrated as having an C-shaped base portion 908, 908' and a plurality of spikes 910, 910' protruding from the circumference of the base. The prosthesis 900, 900' also includes a buttress 912, 912' that extends from an arc of the base generally radially inwardly for a first axial part and then turns radially outwardly for a second axial part.

FIG. 26 illustrates a prosthesis 920 having a C-shaped base portion implanted from an implanter device 922 at an annulus 924 of a mitral valve 926 in accordance with an aspect of the present invention. The mitral valve 926 includes a functional anterior leaflet 932 that extends from the annulus 924. A damaged or defective posterior leaflet 936 is shown between a posterior side of a buttress 938 of the prosthesis 920; although the posterior leaflet could be removed. Spikes 940 are illustrated extending from the posterior side of the buttress 938 and engaging and/or penetrating the posterior leaflet 936, which helps maintain the prosthesis in a desired position and orientation relative to the patient's valve 926. The prosthesis 920 also includes other spikes 942 that protrude generally radially from a base portion 944 of the prosthesis, such as described herein, for engaging and/or penetrating surrounding tissue at the annulus 924.

As mentioned above, the buttress 938 extends axially from an arc of the base portion 944 radially inwardly for a first part of its length and then curves radially outwardly for a second part of its length. Thus, at least a portion of the buttress 938 extends into the ventricle generally toward the anterior leaflet 932. With such configuration, the anterior leaflet 932 can move into and out of engagement with the anterior surface of the leaflet, thereby controlling the flow of blood through the valve 926. As a result of the cooperation between the leaflet 932 and the anterior surface of the buttress 938, unidirectional flow of blood can be provided through the valve 926 and the prosthesis 920 in accordance with an aspect of the present invention.

Figure 27:
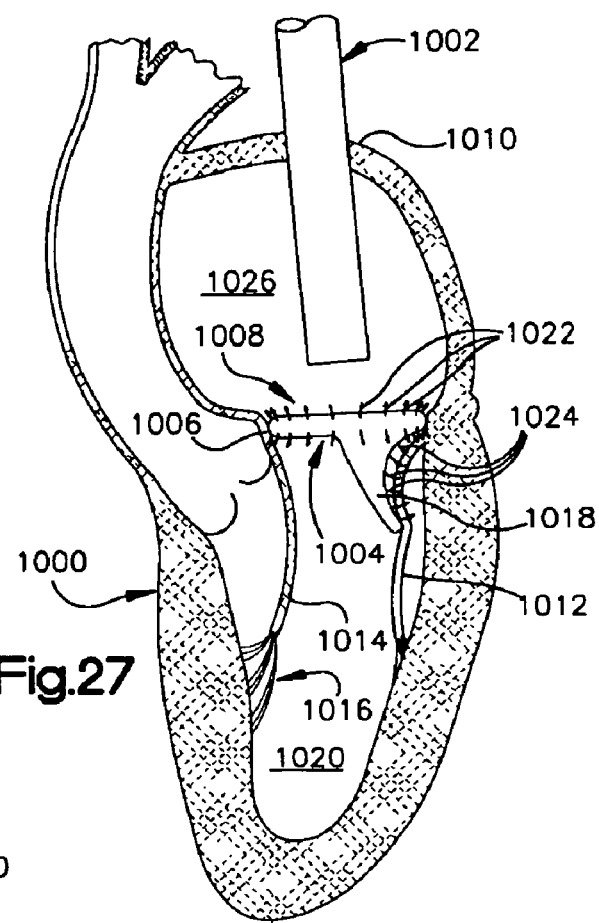
FIG. 27 is an example of a prosthesis being implanted in accordance with an aspect of the present invention.
Figure 28:
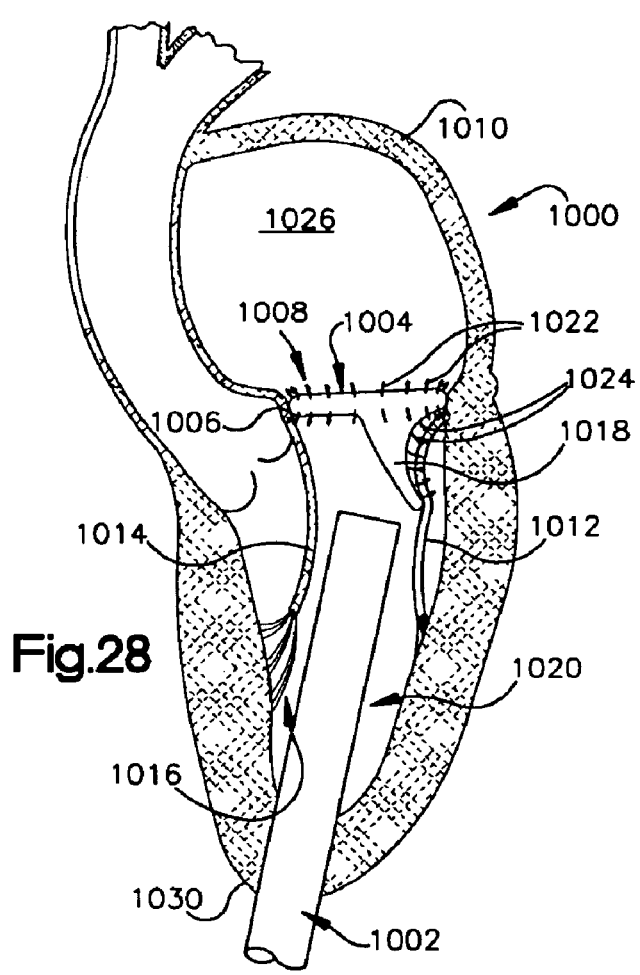
FIG. 28 is another example of a prosthesis being implanted in accordance with an aspect of the present invention.

FIGS. 27 and 28 illustrate part of a heart 1000 in which an implantation device 1002 is utilized to implant a prosthesis 1004 at an annulus 1006 of a mitral valve 1008 to help improve operation of the valve in accordance with an aspect of the present invention. FIGS. 27 and 28 illustrate two possible approaches that can be utilized to position and implant the prosthesis 1004 at the mitral valve 1008.

In FIG. 27, the prosthesis 1004 is implanted at the annulus 1006 by positioning a barrel of the implanter device 1002 through the left atrial wall 1010. In this example, it is assumed that the posterior leaflet 1012 of the mitral valve 1008 is defective and that the anterior leaflet 1014 is functional. The anterior leaflet 1014 that extends from the annulus 1006 adjacent the aortic opening and attaches to the muscuilar tissue in the wall of the left ventricle by fibrous cordae tendonae 1016. The prosthesis 1004 includes a buttress 1018 that extends axially and radially inwardly for a first part of its length and then turns outwardly for a second part of its length. Thus, when prosthesis 1004 is implanted at the annulus and expands to its expanded condition, the buttress 1018 extends into the left ventricle 1020 interposed between the posterior and anterior leaflets 1012 and 1014. For example, where the prosthesis 1004 is formed using a frame of a shape memory alloy (e.g., nitinol) or other resilient material, it will automatically expand when discharged from the barrel, such that its base portion engages surrounding tissue at the annulus 1006.

As mentioned above, the prosthesis 1004 also includes protruding features (e.g., spikes) 1022 that extend from a base portion of the prosthesis. The spikes 1022 can engage and/or penetrate the surrounding tissue at the annulus 1006 of the valve 1008 so as to maintain the position and angular orientation of the prosthesis relative to the valve. Another set of spikes 1024 can also extend from a posterior side of the buttress 1018, which can engage and/or penetrate the posterior leaflet 1012 to further help maintain the position and orientation of the prosthesis 1004. It is to be appreciated that the spikes 1022, 1024 enable the prosthesis 1004 to be implanted without sutures; although sutures could be applied to further help secure the prosthesis to the heart.

It is to be appreciated that the buttress 1018 may be formed of a generally rigid material that remains substantially stationary (e.g., static) during both systole and diastole. A desired stiffness for the buttress 1018 can be provided, for example, by using different materials or employing a tighter mesh for its base portion or buttress support frame.

When implanted, the buttress 1018 simulates the function of the posterior leaflet at systole by providing a surface against which the anterior leaflet 1014 can substantially coapt. As a result, the buttress 1018 and the anterior leaflet 1014 cooperate to inhibit regurgitation of blood from the left ventricle 1020 into the left atrium 1026, such as during ventricular contraction at systole. The buttress 1018 in conjunction with the anterior leaflet 1014 also facilitates and promotes unidirectional flow of blood at diastole. In particular, an opening or aperture extends through the implanted apparatus 1004 between the buttress 1018 and the anterior leaflet 1014. Advantageously, the movement of the anterior leaflet 1014 relative to the buttress 1018 (in response to the flow of blood during diastole), provides a sufficient orifice to permit the substantially free flow of blood from the left atrium 1026 into the left ventricle 1020. The arcuate base portion (e.g., annular or generally C-shaped) of the apparatus 1004 further may help support the annulus 1006 of the mitral valve 1008 at systole to promote the desired coaptation between the buttress 1018 and the anterior leaflet 1014.

FIG. 28 is similar to FIG. 27, but the prosthesis 1004 is depicted as being implanted from a barrel of an implantation device 1002 that has been inserted through an apex 1030 of the patient's heart 1000. For purposes of ease of explanation, identical reference numbers are used in FIG. 28 to refer to corresponding parts previously identified in FIG. 27. It will be appreciated that the orientation of the inflow and outflow ends of the prosthesis 1004 within the barrel of the implantation device 1002 will be different depending on the direction from which the barrel approaches the implantation site.

While the examples in FIGS. 27 and 28 show a generally cylindrical barrel of the implantation device 1002 for more direct (e.g., generally linear) implantation, it is to be understood that the barrel could also form part of a catheter system or other type of implantation system, which can be inserted into the heart to navigate the prosthesis 1004 at a desired position. For example, the barrel can travel through the vascular system to position the prosthesis 1004 at any desired position for implantation. It will be understood and appreciated that, according to one or more aspects of the present invention, a catheter system can cause the barrel to travel along other paths into the heart (e.g., through the pulmonary artery, pulmonary vein, aorta, or innominate veins) as well as can be used to implant a prosthesis at other heart valves, such as at the tricuspid valve, the aortic valve, and the pulmonic valve. It further will be appreciated that implantation of the prosthesis 1002 can be performed with the assistance of suitable imaging equipment (not shown), such as x-ray, ultrasound, or other imaging devices. The imaging equipment helps the surgeon navigate the barrel and the prosthesis to the desired position.

In the examples of FIGS. 27 and 28, for purposes of brevity, the prosthesis 1004 is depicted as a having an annular base portion, although a prosthesis having a generally C-shaped base portion also could be utilized in accordance with an aspect of the present invention.

In view of the foregoing, an apparatus according to the present invention provides a useful repair apparatus for helping to improve operation of a patient's heart valve. The apparatus may be employed to both support a heart valve annulus and mitigate problems associated with coaptation and/or lesions in a leaflet by providing a buttress with which one or more leaflets may move into and out of engagement. The apparatus further provides a simplified repair option (implanting a device at an annulus of a heart valve) when compared with other, more conventional methods of reconstruction and repair.

Additionally, a generally sutureless implantation of the prosthesis can be implemented. This can be done with little or no cardio pulmonary bypass, such as may depend on the condition of the patient. By way of example, where a patient experiences sudden regurgitation resulting in severe pulmonary edema, pulmonary bypass may not be an acceptable option. In such circumstances, a minithoracotomy can be performed to provide an opening for positioning a barrel of an implantation device at a desired position in the patient's heart and, in turn, to implant a prosthesis in accordance with an aspect of the present invention. The prosthesis can provide a permanent or temporary solution, such as to stabilize the patient until the patient can better withstand the stresses of more rigorous surgery, such as may include cardio pulmonary bypass. As a result, a significant amount of time may be saved with less stress on the patient, thereby mitigating the risks of morbidity and mortality associated with open-heart surgery typically employed to implant a heart valve prosthesis.

It is to be appreciated by those skilled in the art that, while many of the illustrated examples show the apparatus for treating a bicuspid (mitral) valve, an apparatus in accordance with the present invention can also be used for repairing other types of heart valves (e.g., a tricuspid valve or other bicuspid valves). In addition, an apparatus may in accordance with the present invention, be implanted from either the inflow side or outflow side of a heart valve annulus.

What has been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising."

What is claimed is:

1. An apparatus for helping improve operation of a heart valve, comprising:

a generally arcuate base portion; and a buttress extending from the base portion generally axially and inwardly relative to the base portion so as to permit substantially bi-directional flow of fluid relative to the apparatus, a surface of the buttress being dimensioned and configured to simulate a leaflet at systole that is to be engaged by at least one leaflet of the heart valve when the apparatus is implanted at the heart valve, the base portion and the buttress being configured to provide a cross-sectional dimension that is variable between a reduced cross-sectional dimension to facilitate implantation thereof and an expanded cross-sectional dimension that helps maintain a desired position of the apparatus when implanted at the heart valve, whereby substantially unidirectional flow of blood is provided when the apparatus is implanted at the heart valve.

2. The apparatus of claim 1, the base portion further comprising a generally C-shaped base portion having a curved length between opposed ends of the C-shaped base portion, the buttress extending from an arc portion of the C-shaped base portion intermediate the opposed ends thereof.

3. The apparatus of claim 2, the buttress extending a first length in a direction radially inwardly and axially from the base portion and then curving outwardly for a second length to terminate in a distal end thereof.

4. The apparatus of claim 1, the arcuate base portion further comprising an annular ring and an aperture extends through the apparatus between the buttress and an opposed side of the annular base portion so as to permit substantially bi-directional flow of fluid axially relative to the apparatus.

5. The apparatus of claim 1, further comprising an outer sheath of a substantially flexible material covering at least the surface of the buttress.

6. The apparatus of claim 5, the outer sheath completely covering the buttress and the base portion.

7. The apparatus of claim 6, wherein the flexible material comprises a substantially biocompatible animal tissue material.

8. The apparatus of claim 7, the biocompatible animal tissue material comprises animal pericardium.

9. The apparatus of claim 6, further comprising a plurality of features extending through the outer sheath generally radially from the base portion to help maintain the apparatus at a desired position relative to the heart valve when implanted.

10. The apparatus of claim 1, the base portion being formed of a shape memory alloy material operative to urge the prosthesis to the expanded cross-sectional dimension.

11. The apparatus of claim 10, the buttress further being formed of the shape memory alloy material.

12. The apparatus of claim 1, further comprising features that extend outwardly from the base portion to help maintain the apparatus at a desired position and orientation relative to the heart valve when implanted.

13. The apparatus of claim 12, the base portion being formed of a mesh material with triangular projections at the inflow and outflow ends of the base portion, the triangular projections extending outwardly from the base portion to define the features.

14. The apparatus of claim 12, the features extending different lengths from the base portion according to their relative position along the base portion.

15. The prosthesis of claim 1, in combination with a retaining member to retain the apparatus in the reduced cross-sectional condition.

16. The apparatus of claim 15, wherein the retaining member includes a barrel in which at least a substantial portion of the apparatus is disposed to maintain the apparatus in the reduced cross-sectional condition.

17. The apparatus of claim 16, wherein the barrel comprises part of a catheter system adapted to position an opening of the barrel at a desired position and to discharge the prosthesis from the enclosure, such that the apparatus expands toward the expanded cross-sectional condition.

18. The apparatus of claim 1 in combination with an implanter, the combination comprising:

the implanter comprising an elongated generally cylindrical barrel dimensioned and configured to receive the apparatus when in the reduced cross-sectional condition; and the apparatus being disposed within the cylindrical barrel, such that an inner sidewall of the cylindrical barrel maintains the prosthesis in the second condition.

19. The appartus of claim 18, wherein the implanter further comprises a plunger operative to move within the cylindrical barrel and urge the apparatus out of the cylindrical barrel, the apparatus being configured to expand from the reduced cross-sectional condition to the first condition when discharged from the cylindrical barrel.

20. An apparatus for helping improve operation of a heart valve, comprising:

a frame comprising a generally arcuate base portion and a support portion extending from the base portion generally axially and inwardly so as to permit substantially bi-directional flow of fluid relative to the apparatus, the support portion terminating at a distal end spaced from the base portion, the frame being formed of a material that enables a cross-sectional dimension of the apparatus to be variable between a reduced cross-sectional dimension, which facilitates implantation of the apparatus, and an expanded cross-sectional dimension that helps maintain the apparatus at a desired position when the apparatus is implanted at the heart valve; and a web of a substantially flexible material extending from an arc of the base portion and supported by the support portion of the frame to define a buttress dimensioned and configured to simulate a leaflet at systole that is to be engaged by at least one leaflet of the heart valve, whereby, when the apparatus is implanted at the heart valve, at least one leaflet of the heart valve is moveable relative to a surface of the web so as to provide for substantially unidirectional blood flow relative to the apparatus.

21. The apparatus of claim 20, the base portion further comprises a generally C-shaped base portion having a curved length between opposed ends of the C-shaped base portion, the buttress extending from an arc portion of the C-shaped base portion intermediate the opposed ends thereof.

22. The apparatus of claim 20, the base portion further comprises ring and an aperture extends through the apparatus between the buttress and an opposed side of the annular base portion.

23. The apparatus of claim 20, the web of flexible material further comprising a substantially biocompatible animal tissue.

24. The apparatus of claim 23, wherein the biocompatible animal tissue is animal pericardium.

25. The apparatus of claim 20, the frame further comprising a mesh material that is deformable to the reduced cross-sectional condition and expandable to the expanded cross-sectional condition.

26. The apparatus of claim 25, the mesh material further comprising material having shape memory properties.

27. An apparatus for helping improve operation of a defective heart valve having at least one viable leaflet, comprising:

means for supporting an annulus of the heart valve so as to permit bi-directional blood flow through the support means, the support means being deformable to a reduced cross-sectional condition and expandable from the reduced cross-sectional condition to an expanded cross-sectional condition; and means for simulating a leaflet at systole and for substantially coapting with the at least one leaflet of the heart valve when the apparatus is attached at the annulus of the heart valve, such that the at least one leaflet is moveable into and out of engagement with the means for substantially coapting to provide for substantially unidirectional blood flow relative to the apparatus, the means for simulating extending from the means for supporting.

28. The apparatus of claim 27, further comprising means for helping maintain the position of the apparatus relative to the heart valve, the means for helping extending from the support means.

29. A method for helping improve operation of a patient's heart valve, comprising:

positioning an apparatus within a barrel so as to have a reduced cross-sectional condition, the apparatus comprising a base portion and a support extending from at least a portion of the base;

urging the apparatus from the barrel to implant the apparatus at the patient's heart valve;

expanding the apparatus to an expanded condition at the patient's heart valve, such that the apparatus simulates a leaflet at systole, such that at least one leaflet of the patient's heart valve is moveable into and out of engagement with the apparatus to provide for substantially unidirectional flow of blood.

30. The method of claim 29, wherein prior to urging the apparatus from the barrel, the method further comprises navigating the barrel to a location near an annulus of the patient's heart valve.

31. The method of claim 29, the expansion of the apparatus occurring in response to a stimulus or automatically upon urging the apparatus from the barrel.

* * * * *